(12) United States Patent
Enan

(10) Patent No.: US 8,685,471 B2
(45) Date of Patent: Apr. 1, 2014

(54) COMPOSITIONS AND METHODS FOR CONTROLLING INSECTS

(75) Inventor: Essam Enan, Nashville, TN (US)

(73) Assignee: Tyratech, Inc., Morrisville, NC (US)

( * ) Notice: Subject to any disclaimer, the term of this patent is extended or adjusted under 35 U.S.C. 154(b) by 0 days.

(21) Appl. No.: 11/879,567

(22) Filed: Jul. 17, 2007

(65) Prior Publication Data

US 2008/0020078 A1    Jan. 24, 2008

Related U.S. Application Data

(60) Provisional application No. 60/807,600, filed on Jul. 17, 2006.

(51) Int. Cl.
*A61K 36/53* (2006.01)
*A61K 36/00* (2006.01)

(52) U.S. Cl.
USPC ............ 424/745; 424/725; 424/776; 424/777

(58) Field of Classification Search
None
See application file for complete search history.

(56) References Cited

U.S. PATENT DOCUMENTS

| | | |
|---|---|---|
| 3,943,063 A | 3/1976 | Morishita et al. |
| 3,971,852 A | 7/1976 | Brenner et al. |
| 4,211,668 A | 7/1980 | Tate |
| 4,278,658 A | 7/1981 | Hooper et al. |
| 4,320,113 A | 3/1982 | Kydonieus |
| 4,434,181 A | 2/1984 | Marks et al. |
| 4,551,480 A | 11/1985 | Stiefel et al. |
| 4,678,775 A | 7/1987 | Nathanson |
| 4,693,890 A | 9/1987 | Wilson et al. |
| 4,696,676 A | 9/1987 | Wilson et al. |
| 4,748,860 A | 6/1988 | Butler et al. |
| 4,759,228 A | 7/1988 | Butler et al. |
| 4,762,718 A | 8/1988 | Marks, Sr. |
| 4,764,367 A | 8/1988 | Wilson et al. |
| 4,783,457 A | 11/1988 | Nathanson |
| 4,801,446 A | 1/1989 | Wilson et al. |
| 4,801,448 A | 1/1989 | Wilson et al. |
| 4,808,403 A | 2/1989 | Wilson et al. |
| 4,816,248 A | 3/1989 | Wilson et al. |
| 4,818,526 A | 4/1989 | Wilson et al. |
| 4,859,463 A | 8/1989 | Wilson et al. |
| 4,876,087 A | 10/1989 | Wilson et al. |
| 4,880,625 A | 11/1989 | Wilson et al. |
| 4,885,855 A | 12/1989 | Marks et al. |
| 4,886,662 A | 12/1989 | Wilson et al. |
| 4,892,871 A | 1/1990 | Nathanson |
| 4,902,504 A | 2/1990 | Wilson et al. |
| 4,902,690 A | 2/1990 | Nathanson |
| 4,911,906 A | 3/1990 | Wilson et al. |
| 4,943,435 A | 7/1990 | Baker et al. |
| 4,959,209 A | 9/1990 | Wilson et al. |
| 4,970,068 A | 11/1990 | Wilson et al. |
| 4,988,507 A | 1/1991 | Wilson et al. |
| 4,988,508 A | 1/1991 | Wilson et al. |
| 4,988,509 A | 1/1991 | Wilson et al. |
| 4,990,684 A | 2/1991 | Hoelderich et al. |
| 4,992,270 A | 2/1991 | Wilson et al. |
| 5,091,423 A | 2/1992 | Wilson et al. |
| 5,106,622 A | 4/1992 | Sherwood et al. |
| 5,110,594 A | 5/1992 | Morita |
| 5,118,711 A | 6/1992 | Wilson et al. |
| 5,126,369 A | 6/1992 | Wilson et al. |
| 5,134,892 A | 8/1992 | Wilson et al. |
| 5,165,926 A | 11/1992 | Wilson et al. |
| 5,175,175 A | 12/1992 | Wilson et al. |
| 5,190,745 A * | 3/1993 | Dohara et al. .................. 424/45 |
| 5,196,200 A | 3/1993 | Wilson et al. |
| 5,204,372 A | 4/1993 | Wilson et al. |
| 5,205,065 A | 4/1993 | Wilson et al. |
| 5,228,233 A | 7/1993 | Butler et al. |
| 5,250,575 A | 10/1993 | Wilson et al. |
| 5,272,179 A | 12/1993 | Butler et al. |
| 5,281,621 A | 1/1994 | Wilson et al. |
| 5,321,048 A | 6/1994 | Wilson et al. |
| 5,327,675 A | 7/1994 | Butler et al. |
| 5,344,776 A | 9/1994 | Venter et al. |
| 5,344,847 A | 9/1994 | Wilson et al. |
| 5,354,783 A | 10/1994 | Marin et al. |
| 5,366,975 A | 11/1994 | Nathanson |
| 5,387,418 A | 2/1995 | Marin et al. |
| 5,401,500 A | 3/1995 | Warren et al. |
| 5,407,609 A | 4/1995 | Tice et al. |
| 5,409,958 A | 4/1995 | Butler et al. |
| 5,417,009 A | 5/1995 | Butler et al. |

(Continued)

FOREIGN PATENT DOCUMENTS

| | | |
|---|---|---|
| CN | 1122703 A | 5/1996 |
| CN | 1 481 849 | 3/2004 |

(Continued)

OTHER PUBLICATIONS

Translation of CN 1481849 A—2004.*
Notice of Reason for Rejection, mailed in related Japanese Patent Application No. 2009-520814, dated Oct. 30, 2012.
State Intellectual Property Office of China, First Office Action issued in corresponding Chinese application No. 200780026844.1, mailed Mar. 7, 2012, 7 pages.
European Patent Office, European Search Report issued in corresponding European application No. 07836120.1, mailed on May 30, 2012, 9 pages.
Hammack, Leslie, "Single and Blended Maize Volatiles as Attractants for Diabroticite Corn Rootworm Beetles," Journal of Chemical Ecology, Jul. 31, 2001, pp. 1373-1390, vol. 27, No. 7.

(Continued)

*Primary Examiner* — Chris R Tate
*Assistant Examiner* — Russell Fiebig
(74) *Attorney, Agent, or Firm* — Davis Wright Tremaine LLP

(57) ABSTRACT

Pest control compositions, blends, and formulations are disclosed. The blends contain, in a synergistic combinations, at least two ingredients such as Lilac Flower Oil, D-Limonene, Thyme Oil, Lime Oil, Black Seed Oil, Wintergreen Oil, Linalool, Tetrahydrolinalool, Vanillin, Isopropyl myristate, Piperonal (aldehyde), Geraniol, Geraniol 60, Triethyl Citrate, and Methyl Salicylate.

13 Claims, No Drawings

(56) References Cited

U.S. PATENT DOCUMENTS

| | | |
|---|---|---|
| 5,418,010 A | 5/1995 | Janda et al. |
| 5,439,690 A | 8/1995 | Knight et al. |
| 5,439,941 A | 8/1995 | Butler et al. |
| 5,441,988 A | 8/1995 | Butler et al. |
| 5,447,714 A | 9/1995 | Marin et al. |
| 5,449,695 A | 9/1995 | Marin et al. |
| 5,458,882 A | 10/1995 | Marin et al. |
| 5,464,626 A | 11/1995 | Warren et al. |
| 5,472,701 A | 12/1995 | Warren et al. |
| 5,474,898 A | 12/1995 | Venter et al. |
| 5,521,165 A | 5/1996 | Warren et al. |
| 5,576,010 A | 11/1996 | Warren et al. |
| 5,576,011 A | 11/1996 | Butler et al. |
| 5,593,600 A | 1/1997 | Solomon |
| 5,633,236 A | 5/1997 | Warren et al. |
| 5,635,173 A | 6/1997 | Warren et al. |
| 5,635,174 A | 6/1997 | Warren et al. |
| 5,665,781 A | 9/1997 | Warren et al. |
| 5,683,687 A | 11/1997 | Marin et al. |
| 5,693,344 A | 12/1997 | Knight et al. |
| 5,703,104 A | 12/1997 | Peck et al. |
| 5,753,686 A | 5/1998 | Marin et al. |
| 5,772,983 A | 6/1998 | O'Connell et al. |
| 5,785,982 A | 7/1998 | Warren et al. |
| 5,814,325 A | 9/1998 | Rod |
| 5,827,584 A | 10/1998 | Akao et al. |
| 5,840,669 A | 11/1998 | Neelakantan |
| 5,849,317 A | 12/1998 | Shorey et al. |
| 5,855,903 A | 1/1999 | Warren et al. |
| 5,942,214 A | 8/1999 | Lucas et al. |
| 5,956,865 A | 9/1999 | Durance et al. |
| 5,980,931 A | 11/1999 | Fowler et al. |
| 5,990,178 A | 11/1999 | Ninkov |
| 5,998,484 A | 12/1999 | Zobitne et al. |
| 6,001,874 A | 12/1999 | Veierov |
| 6,004,569 A | 12/1999 | Bessette et al. |
| 6,006,470 A | 12/1999 | Geoghegan et al. |
| 6,024,874 A | 2/2000 | Lott |
| 6,114,384 A | 9/2000 | Bessette et al. |
| 6,130,253 A | 10/2000 | Franklin et al. |
| 6,143,288 A | 11/2000 | Warren et al. |
| 6,183,767 B1 | 2/2001 | Bessette et al. |
| 6,238,682 B1 | 5/2001 | Klofta et al. |
| 6,255,356 B1 | 7/2001 | Butler |
| 6,272,790 B1 | 8/2001 | Paganessi et al. |
| 6,322,825 B1 | 11/2001 | Ninkov |
| 6,329,433 B1 | 12/2001 | Bessette et al. |
| 6,331,572 B1 | 12/2001 | Bessette et al. |
| 6,333,302 B1 | 12/2001 | Beer et al. |
| 6,333,360 B1 | 12/2001 | Bessette et al. |
| 6,340,710 B1 | 1/2002 | Bessette et al. |
| 6,342,535 B1 | 1/2002 | Bessette et al. |
| 6,342,536 B1 | 1/2002 | Bessette et al. |
| 6,360,477 B1 | 3/2002 | Flashinski et al. |
| 6,368,508 B1 | 4/2002 | Gatz et al. |
| 6,372,801 B1 | 4/2002 | Bessette et al. |
| 6,372,803 B1 | 4/2002 | Bessette et al. |
| 6,376,556 B1 | 4/2002 | Bessette et al. |
| 6,395,789 B1 | 5/2002 | Bessette et al. |
| 6,414,036 B1 | 7/2002 | Ninkov |
| 6,451,844 B1 | 9/2002 | Watkins et al. |
| 6,506,707 B1 | 1/2003 | Bessette |
| 6,531,163 B1 | 3/2003 | Bessette et al. |
| 6,534,099 B1 | 3/2003 | Bessette et al. |
| 6,548,085 B1 | 4/2003 | Zobitne et al. |
| 6,555,121 B1 | 4/2003 | Bessette et al. |
| 6,610,254 B1 | 8/2003 | Furner et al. |
| 6,649,660 B2 | 11/2003 | Ninkov |
| 6,660,288 B2 | 12/2003 | Behan et al. |
| 6,670,311 B1 | 12/2003 | Aldcroft et al. |
| 6,689,395 B2 | 2/2004 | Bessette |
| 6,713,518 B1 | 3/2004 | Bessette et al. |
| 6,812,258 B2 | 11/2004 | Bessette et al. |
| 6,841,577 B2 | 1/2005 | Bessette et al. |
| 6,844,369 B2 | 1/2005 | Ninkov |
| 6,849,614 B1 | 2/2005 | Bessette et al. |
| 6,858,653 B1 | 2/2005 | Bessette |
| 6,887,899 B1 | 5/2005 | Bessette |
| 6,921,539 B2 | 7/2005 | Ninkov |
| 6,949,587 B1 | 9/2005 | Bessette |
| 6,969,522 B2 | 11/2005 | Bessette |
| 6,974,584 B2 | 12/2005 | Bessette |
| 6,986,898 B1 | 1/2006 | Bessette |
| 7,008,649 B2 | 3/2006 | Bessette et al. |
| 7,109,240 B2 | 9/2006 | Bessette et al. |
| 7,157,411 B2 | 1/2007 | Rohde et al. |
| 7,201,926 B2 | 4/2007 | Fried et al. |
| 7,208,519 B2 | 4/2007 | Ninkov |
| 7,238,726 B2 | 7/2007 | Bessette |
| 7,238,798 B2 | 7/2007 | Lee et al. |
| 7,241,806 B2 | 7/2007 | Bessette |
| 7,250,175 B2 | 7/2007 | Bessette et al. |
| 7,291,650 B2 | 11/2007 | Bessette et al. |
| 7,320,966 B2 | 1/2008 | Bessette et al. |
| 7,351,420 B2 | 4/2008 | Bessette et al. |
| 7,357,939 B2 | 4/2008 | Bessette |
| 7,361,366 B2 | 4/2008 | Bessette et al. |
| 7,381,431 B2 | 6/2008 | Baker et al. |
| 7,541,155 B2 | 6/2009 | Enan |
| 7,622,269 B2 | 11/2009 | Enan |
| 2002/0028256 A1 | 3/2002 | Bessette |
| 2002/0034556 A1 | 3/2002 | Khazan |
| 2002/0073928 A1 | 6/2002 | Ingman et al. |
| 2002/0076360 A1 | 6/2002 | Ingman et al. |
| 2002/0081230 A1 | 6/2002 | Ingman et al. |
| 2002/0096121 A1 | 7/2002 | Ingman et al. |
| 2002/0107287 A1 | 8/2002 | Bessette et al. |
| 2003/0026823 A1 | 2/2003 | Fried et al. |
| 2003/0036530 A1 | 2/2003 | Bessette |
| 2003/0039674 A1 | 2/2003 | Bessette |
| 2003/0091531 A1 | 5/2003 | Kensek |
| 2003/0091657 A1 | 5/2003 | Chiasson |
| 2003/0091661 A1 | 5/2003 | Bessette |
| 2003/0108622 A1 | 6/2003 | Bessette et al. |
| 2003/0108623 A1 | 6/2003 | Bessette et al. |
| 2003/0175369 A1 | 9/2003 | Khazan-Enache |
| 2003/0194454 A1* | 10/2003 | Bessette et al. ............... 424/745 |
| 2004/0146595 A1 | 7/2004 | Bessette et al. |
| 2004/0156922 A1 | 8/2004 | Bessette et al. |
| 2004/0185080 A1 | 9/2004 | Hojo et al. |
| 2004/0192551 A1 | 9/2004 | Bessette |
| 2004/0213822 A1 | 10/2004 | Birch et al. |
| 2004/0248791 A1 | 12/2004 | Spana et al. |
| 2005/0004233 A1 | 1/2005 | Bessette et al. |
| 2005/0008714 A1* | 1/2005 | Enan ............................ 424/745 |
| 2005/0013885 A1 | 1/2005 | Chiasson |
| 2005/0019269 A1 | 1/2005 | Marks et al. |
| 2005/0070576 A1 | 3/2005 | Spooner-Hart et al. |
| 2005/0136089 A1 | 6/2005 | Bessette et al. |
| 2005/0143260 A1 | 6/2005 | Bessette et al. |
| 2005/0147636 A1 | 7/2005 | Bessette et al. |
| 2005/0163869 A1 | 7/2005 | Bessette et al. |
| 2005/0170024 A1 | 8/2005 | Bessette et al. |
| 2005/0170025 A1 | 8/2005 | Bessette et al. |
| 2005/0170026 A1 | 8/2005 | Bessette et al. |
| 2005/0214267 A1 | 9/2005 | Enan |
| 2005/0249768 A1 | 11/2005 | Fried et al. |
| 2005/0260241 A1 | 11/2005 | Bessette et al. |
| 2005/0260242 A1 | 11/2005 | Bessette et al. |
| 2005/0288227 A1 | 12/2005 | Marks et al. |
| 2006/0083763 A1 | 4/2006 | Neale et al. |
| 2006/0088564 A1 | 4/2006 | Bessette |
| 2006/0115507 A1 | 6/2006 | Bessette |
| 2006/0115508 A1 | 6/2006 | Bessette |
| 2006/0115509 A1 | 6/2006 | Bessette |
| 2006/0115510 A1 | 6/2006 | Bessette |
| 2006/0121074 A1 | 6/2006 | Bessette |
| 2006/0263403 A1 | 11/2006 | Enan |
| 2007/0009616 A1 | 1/2007 | Marks |
| 2007/0098750 A1 | 5/2007 | Bessette |
| 2007/0178128 A1 | 8/2007 | Bessette |
| 2007/0190094 A1 | 8/2007 | Bessette |
| 2007/0207221 A1 | 9/2007 | Bessette et al. |
| 2007/0298131 A1 | 12/2007 | Bessette et al. |

(56) References Cited

U.S. PATENT DOCUMENTS

| | | |
|---|---|---|
| 2007/0299037 A1 | 12/2007 | Bessette et al. |
| 2007/0299038 A1 | 12/2007 | Bessette et al. |
| 2008/0003315 A1 | 1/2008 | Bessette et al. |
| 2008/0003316 A1 | 1/2008 | Bessette et al. |
| 2008/0003317 A1 | 1/2008 | Bessette et al. |
| 2008/0004240 A1 | 1/2008 | Bessette et al. |
| 2008/0015167 A1 | 1/2008 | Bessette et al. |
| 2008/0015249 A1 | 1/2008 | Bessette et al. |
| 2008/0020381 A1 | 1/2008 | Henrich et al. |
| 2008/0032387 A1 | 2/2008 | Bailey et al. |
| 2008/0038383 A1 | 2/2008 | Bessette et al. |
| 2008/0075796 A1 | 3/2008 | Enan |
| 2008/0131533 A1 | 6/2008 | Kvitnitsky et al. |
| 2008/0153904 A1 | 6/2008 | Bessette |
| 2009/0232918 A1 | 9/2009 | Enan |

FOREIGN PATENT DOCUMENTS

| | | | |
|---|---|---|---|
| CN | 1481849 A | * | 3/2004 |
| CN | 1631169 | | 6/2005 |
| EP | 1 146 111 | | 10/2001 |
| JP | H1-301607 A | | 12/1989 |
| JP | H2-207004 A | | 8/1990 |
| JP | H3-7210 A | | 1/1991 |
| JP | H3-285993 A | | 12/1991 |
| JP | H5-208902 A | | 8/1993 |
| JP | H6-345613 A | | 12/1994 |
| JP | H9-500367 T | | 1/1997 |
| JP | H9-227305 A | | 9/1997 |
| JP | H10-152407 A | | 6/1998 |
| JP | H11-171703 A | | 6/1999 |
| JP | H11-279583 A | | 10/1999 |
| JP | 2000-166399 A | | 6/2000 |
| JP | 2000-513027 T | | 10/2000 |
| JP | 2001-294505 A | | 10/2001 |
| JP | 2001-519367 T | | 10/2001 |
| JP | 2002-501007 T | | 1/2002 |
| JP | 2002-173407 A | | 6/2002 |
| JP | 2002-521406 T | | 7/2002 |
| JP | 2003-505483 T | | 2/2003 |
| JP | 2003-201203 A | | 7/2003 |
| WO | WO 94/27434 A1 | | 12/1994 |
| WO | WO 98/02044 | | 1/1998 |
| WO | WO 98/054971 A1 | | 12/1998 |
| WO | WO 99/18802 A1 | | 4/1999 |
| WO | WO 99/21891 A1 | | 5/1999 |
| WO | WO 99/33973 A3 | | 7/1999 |
| WO | WO 00/05964 A1 | | 2/2000 |
| WO | WO 00/21364 A2 | | 4/2000 |
| WO | WO 00/50566 A2 | | 8/2000 |
| WO | WO 00/51436 A1 | | 9/2000 |
| WO | WO 00/53020 A1 | | 9/2000 |
| WO | WO 00/75322 A | | 12/2000 |
| WO | WO 01/00020 A1 | | 1/2001 |
| WO | WO 01/00026 A1 | | 1/2001 |
| WO | WO 01/00032 A1 | | 1/2001 |
| WO | WO 01/00033 A1 | | 1/2001 |
| WO | WO 01/00034 A1 | | 1/2001 |
| WO | WO 01/00049 A1 | | 1/2001 |
| WO | WO 01/08496 A1 | | 2/2001 |
| WO | WO 01/10214 A2 | | 2/2001 |
| WO | WO 01/18201 A1 | | 3/2001 |
| WO | WO 01/60163 A2 | | 8/2001 |
| WO | WO 01/91554 A1 | | 12/2001 |
| WO | WO 01/91556 A2 | | 12/2001 |
| WO | WO 01/91560 A2 | | 12/2001 |
| WO | WO 02/13607 | | 2/2002 |
| WO | WO 02/087527 | | 11/2002 |
| WO | WO 03/016477 A | | 2/2003 |
| WO | WO 03/083028 | | 10/2003 |
| WO | WO 2004/006968 A | | 1/2004 |
| WO | WO 2004/100971 A1 | | 11/2004 |
| WO | WO 2005/092016 A2 | | 10/2005 |
| WO | WO 2008/011054 A2 | | 1/2008 |

OTHER PUBLICATIONS

State Intellectual Property of China, Second Office Action issued in corresponding Chinese application No. 200780026844.1, issued Jun. 29, 2012, 8 pages.

Abou El Ele, et al., *Bulletin of High Institute of Public Health*, University of Alexandria, Alexandria, Egypt. 31(1):15-30, 2001. "Insecticidal activity of some essential oils: cAMP mediates effect."

Alvarez-Sanchez, et al., *Microb Pathog.* 28(4):193-202, Apr. 2000. "A novel cysteine proteinase (CP65) of *Trichomonas vaginalis* involved in cytotoxicity."

Aoyama, et al., *Arch Insect Biochem Physiol.*, 47(1):1-7, May 2001. "Substituent-dependent, positive and negative modulation of *Bombyx mori* adenylate cyclase by synthetic octopamine/tyramine analogues."

Arakawa, et al., *Neuron*. 4(3):343-354, Mar. 1990. "Cloning, localization, and permanent expression of a *Drosophila* octopamine receptor."

Baxter, et al., *Insect Biochem Mol Biol.* 29(5):461-467, May 1999. "Isolation of a cDNA for an octopamine-like, G-protein coupled receptor from the cattle tick, *Boophilus microplus*."

Bekele, et al., "Blend effects in the toxicity of the essential oil constituents of *Ocimum kilimandscharicum* and *Ocimum kenyense* (Labiatae) on two post-harvest insect pests." *Medicinal & Aromatic Plants Abstracts, Resources*, New Delhi, India—New Delhi, vol. 23, No. 6; Dec. 1, 2001.

Berntzen, et al., *J Parasitol.* 51(2):235-242, Apr. 1965. "In vitro hatching of oncosphere of *Hymenolepidid cestodes*."

Bischof, et al., *Insect Biochem Mol Biol.* 34(6):511-521, Jun. 2004. "Cloning, expression and functional anlaysis of an octopamine receptor from *Periplaneta americana*."

Blenau, et al., *J Neurochem.* 74(3):900-908, Mar. 2000. "Amtyr1: characterization of a gene from honeybee (*Apis mellifera*) brain encoding a functional tyramine receptor."

Blenau, et al., *Archives of Insect Biochemistry and Physiology*. 48(1): 13-38, Sep. 2001. "Molecular and Pharmacological Properties of Insect Biogenic Amine Receptors: Lessons From *Drosophilla melanogastor* and *Apis mellifera*."

Borowsky, et al., *Proc Natl Acad Sci USA*. 98(16):8966-8971, Jul. 31, 2001. "Trace amines: Identification of a family of mammalian G protein-coupled receptors."

Bunzow, et al., *Mol Pharmacol* 60(6):1181-1188, Dec. 2001. "Amphetamine, 3,4-Methylenedioxymethamphetamine, Lysergic Acid Diethylamide, and Metabolites of the Cathecholamine Neurotransmitters are Agonists of a Rat Trace Amine Receptor."

Chirgwin, et al., *Biochemistry* 18(24):5294-5299, Nov. 27, 1979. "Isolation of biologically active ribonucleic acid from sources enriched in ribonuclease."

Coats, *Environ Health Prespect.* 87:255-262, 1990. "Mechanisms of toxic action and structure-activity relationships for organochlorine and synthetic pyrethroid insecticides."

Coats, et al., *Naturally occurring pest bioregulators* (Hedin PA, ed), Amer. Chem. Soc., Washington, DC. Chapter 20, pp. 305-316, 1991. "Toxicity neurotoxic effects of monoterpenoids in insects and earthworms."

Colby, *Weeds*. 15(1):20-22, 1967. "Calculating synergistic and antagonistic responses of herbicide combinations."

Cooley L, et al., *Science*, 239(4844):1121-1128, Mar 4, 1998. "Insertional mutagenesis of the *Drosophila* genome with single P elements."

Donini, et al., *J Insect Physiol.* 50(4):3351-361, Apr. 2004. "Evidence for a possible neurotransmitter/neuromodulator role of tyramine on the locust oviducts."

Downer, et al., *Neurochem Res*. 18(12):1245-1248, Dec. 1993. "Characterization of the tyraminergic system in the central nervous system of the locust, *Locusta migratoria* migratoides."

Downer, et al., *Insect Neurochemistry and Neurophysiology* 1993 (Borkovec AB and Loeb MJ, eds), CRC Press, Boca Raton, Florida. pp. 23-38, 1994. "Biogenic amines in insects."

Dudai, et al., *J Neurochem*, 38(6):1551-1558, Jun. 1982. "Aminergic receptors in *Drosophila melanogaster*: properties of [3H]dihydroergocryptine binding sites."

(56) References Cited

OTHER PUBLICATIONS

Dyer, et al. *J Agric Food Chem.* 53(23):9281-9287, 2005. "Fusarium graminearum TRI14 is required for high virulence and DON production on wheat but not for DON synthesis in vitro."

Enan, et al., *Biochem Pharmacol.* 51(4):447-454, Feb. 23, 1996. "Deltamethrin induced thymus atrophy in male Balb/c mice."

Enan, et al., "Insecticidal action of terpenes and phenols to cockroaches: effect on octopamine recetors." International Symposium on Crop Protection, Ghent, Belgium; May 1998.

Enan, "Insecticidal Activity of Essential Oils: Octopaminergic Sites of Action." *Comp. Biochem. Physiol, Part C: Toxicol. & Pharm., Elsevier:* 130(1):325-337, Nov. 1, 2001.

Enan, *Insect Biochem Mol Biol.* 35(4):309-321, 2005. "Molecular response of *Drosophila melanogaster* tyramine receptor cascade to plant essential oils."

EPA, "R.E.D. Facts": *Flowers and Vegetable Oils,* EPA-738-F-93-027, Dec. 1993.

Evans, et al., *Nature,* 287(5777):60-62, Sep. 4, 1980. "Action of formamidine pesticides on octopamine receptors."

Evans, *J Physiol.* 318:99-122, Sep. 1981. "Multiple receptor types for octopamine in the locust."

Evans, et al., *Progress in Brain Research.* 106:259-268, 1995. "Agonist-specific coupling of G-protein-coupled receptors to second-messenger systems."

Finney, *Probit Analysis,* 3rd Ed., Cambridge University Press, London, p. 333, 1971.

Gerhardt, et al., *Molecular Pharmacology,* 51(2):293-300, Feb. 1997. "Molecular Cloning and Pharmacological Characterization of a Molluscan Octopamine Receptor."

Griffin, et al., Eur. J. Pharmacol. 377:117-125, 1999.

Grodnitsky, et al., *J Agric Food Chem.* 50(16):4576-4580, Jul. 31, 2002. "QSAR evaluation of monoterpenoids' insecticidal activity."

Grundy, et al., *Pestic Biochem Physiol.* 23(3):383-388, 1985. "Inhibition of acetylcholinesterases by pulegone-1,2-epoxide."

Gudermann, et al., *Annu Rev Pharmacol Toxicol.* 36:429-459, Apr. 1996. "Diversity and selectivity of receptor-G protein interaction."

Gudermann, et al., *Annu Rev Neurosci.* 20:399-427, Mar. 1997. "Functional and structural complexity of signal transduction via G-protein-coupled receptors."

Guillen, et al., *Life Sci.* 45(7):655-662, 1989. "A possible new class of octopamine receptors coupled to adenylate cyclase in the brain of the dipterous *Ceratitis capitata*. Pharmacological characterization and regulation of 3H-octopamine binding."

Han, et al., *Journal of Neuroscience,* 18(10):3650-3658, May 15, 1998. "A Novel in Octopamine Receptor with Preferential Expression in *Drosophilla* Mushroom Bodies."

Hayashi et al., "The scent substances of pierid butterflies hebomoia-glaucippe and the volatile components of their food plants crataeva-religiosa." Zeitschrift Fuer Naturforschung Section C Journal of Biosciences, vol. 40, No. 1-2, 1985, pp. 47-50.

Hernandez-Sanchez et al., "Attractiveness for *Ceratitis capita* capita (Wiedemann) (Dipt., Tephritidae) of mango (*Mangifera indica,* cv. Tommy Atkins) airborne terpenes," *Journal of Applied Entomology,* vol. 125, No. 4, May 2001, pp. 189-192.

Hiripi, et al., *Brain Res.* 633(1-2):119-126, 1994. "Characterization of tyramine and octopamine receptors in the insect (*Locusta migratoria* migratorioides) brain."

Hori, *Appl Entomol Zool,* 34(3):351-358, 1999. "The Effects of Rosemary and Ginger Oils on the Alighting Behavior of *Myzus persicae* (Sulzer) (Homoptera: Aphididae) and on the Incidence of Yellow Spotted Streak."

Hummelbrunner et al., "Acute, sublethal, antifeedant, and synergistic effects of monoterpenoid essential oil compounds on the tobacco cutworm, *Spodoptera litura* (Lep., Noctuidae)," *Medicinal & Aromatic Plants Abstracts, Resources,* New Delhi, India—_Ne Delhi, vol. 23, No. 4, Aug. 1, 2001.

ISA/US, "International Search Report and the Written Opinion of the International Searching Authority," mailed Jun. 3, 2008 in International Application No. PCT/US07/16255, 6 pages.

Ito, *Parasitology,* 71(3):465-473, Dec. 1975. "In vitro oncospheral agglutination given by immune sera from mice infected and rabbits injected with eggs of *Hymenolepis nana*."

James, et al., *J Chem Ecol.* 30(8):1613-1628, 2004. "Field-testing of methyl salicylate for in recruitment and retention of beneficial insects in grapes and hops."

Janmaat et al., "Enhanced fumigant toxicity of —cyment against Frankliniella occidentalis by simultaneous application of elevated levels of carbon dioxide," *Prest Management Science,* Wiley & Sons, Bognor Regis, GB, vol. 58, Jan. 1,2001, pp. 167-73.

Jurgens et al., "Floral scent compounds of Amazonian Annonaceae species pollinated by small beetles and thrips," *Photochemistry,* Pergamon Press, GB. vol. 55, No. 6, Nov. 1, 2000, pp. 551-558.

Karr, et al., *J Econ Entomol.* 85(2),424-429, 1992. "Effects of four monoterpenoids on growth and reproduction of the German cockroach (Blattodea: Blattellidae)."

Khan, et al., *Arch Insect Biochem Phsiol.* 52(1):7-16, 2003. "Positive and negative modulation of *Bombyx mori* adenylate cyclase by 5-phenyloxazoles: identification of octopamine and tyramine receptor agonists."

Kostyukovsky, et al., *Pest Manag Sci.* 58(11):1101-1106, Nov. 1, 2002. "Activation of octopaminergic receptors by essential oil constituents isoloated from aromatic plants: Possible mode of action against insect pests."

Kravitz, et al., *Neuroscience Symposia.* 1:67-81, 1976. "Octopaine Neurons in Lobsters."

Krymskaya, et al., "Mechanisms of Proliferaiton Synergy by Receptor Tyrosine Kinase and G Protein-Coupled Receptor Activation in Human Airway Smooth Muscle." *AM J Respair Cell mol Biol,* 2000, 23(4):546-554.

Kutsukake, et al., "A tyramine receptor gene mutation causes a defective olfactory behavior in *Drosophila.*" Gene 245:31-42, Mar. 7, 2000.

Kyte, et al., *J Mol Biol.* 157(1):105-132, 1982. "A simple method for displaying the hydropathic character of a protein."

Landolt, et al., *Environ Entomol.* 28(6):954-960, Dec. 1999. "Plant Essential Oils as Arrestants and Repellents for Neonate Larvae of the Codling Moth (Lepidoptera: Tortricidae)."

Lee, et al., *J Econ Entomol.* 90(4):883-892, Aug. 1997. "Insecticidal activity of monoterpenoids to western corn rootworm (Coleoptera: Chrysomelidae), twospotted spider mite (Acari: Tetranychidae), and house fly (Diptera: Muscidae)."

Lee et al., "Fumigant Toxicity of Essential Oils and Nonoterpenes Against the Red Flour Beetle, *Tribolium castaneum* Herbst," *Journal of Asia Pacific Entomolgy, Korean Society of Applied Entomology,* Suwon, KR. vol. 5, No. 2, Nov. 1, 2002, pp. 237-240.

Lomasney, et al., *Proc Natl Acad Sci USA.* 87(13):5094-5098, Jul. 1990. "Expansion of the alpha 2-adrenergic receptor family: cloning and characterization of a human alpha 2-adrenergic receptor subtype, the gene for which is located on chromosome 2."

Lynn, et al., *Cytotechology,* 20(2):3-11, Apr. 11, 1996. "Development and characterization of insect cell lines."

Lynn, et al., *J Insect Sci.* 2:9, May 20, 2002. "Methods for Maintaining Insect Cell Cultures."

Macchioni, et al., Acaricidal Activity of Pine Essential Oils and Their Main Components Against *Tyrophagus* putrescentiae, a Stored Food Mite. *J. Agric. Food. Chem.* 50:4586-4588, 2002.

McCaffery, et al., IRAC Symposium on Insecticide Sustainability: Neonicotinoids ESA Annual Meeting, Dec. 2005. "Effective resistance management for the neonicotinoids: Industry's approach to ensure the continued efficacy of a key insecticide class."

Menevse, et al., *Biochem Biophys Res Com.* 77(2):671-677, 1977. "Evidence for the specific involvement of cyclic AMP in the olfactory transduction mechanism."

Michon, et al., *Mol Biol Evol.* 19(7):1128-1142, Jul. 2002. "Evolutionary relationships of molecules of conserved cysteine-rich motifs in adhesive molecules of malaria parasites."

Miyazawa, et al., *J Agric Food Chem.* 45(3):677-679, Mar. 1997. "Inhibition of Acetylcholinesterase Activity by Monoterpenoids with a p-Menthan Skeleton."

Morty, et al., *J Biol Chem.* 274(37):26149-26156, Sep. 10, 1999. "Oligopeptidase B from *Trypanosoma brucei,* a new member of an emerging subgroup of serine oligopeptidases."

(56) References Cited

OTHER PUBLICATIONS

Muller-Riebau, et al., *J Agric Food Chem.* 43:2262-2266, 1995. "Chemical Composition and Fungitoxic Properties to Phytopathogenic Fungei of Essential Oils of Selected Aromatic Plant Growing Wild in Turkey."
Mundodi, et al., Mol Microbiol. 53(4):1099-1108, 2004. "Silencing the ap65 gene reduces adherence to vaginal epithelial cells by *Trichomonas vaginalis*."
Ngoh, et al., *Pestic Sci.* 54(3):261-268, 1998. "Insecticidal and repellent properties of nine volatile constituents of essential oils against the American cocktoach, *Periplaneta americana* (L.)."
Nok, et al., *Parasitol Res.* 89(4):302-307, Mar. 2003. "Characterization of sialidase from *Entamoaeba hystolitica* and possible pathogenic role in amebiasis."
Ntiamoah et al., "Identity and bioactivity of oviposition deterrents in pine oil for the onion maggot, *Delia antiqua*." Entomologia Experimentalis et Applicata, vol. 79, No. 2, 1996, pp. 219-226.
Ohta, et al., *Insect Mol Biol.* 12(3):217-223, Jun. 2003. "B96Bom encodes a *Bombyx mori* tyramine receptor negatively coupled to adenylate cyclase."
Orchard, *Can J Zool.* 60:659-669, 1982. "Octopamine in insects: neurotransmitter, neurohormone, and neuromodulator."
Pearson, et al., *Ann Intern Med.* 99(2):195-198, Aug. 1983. "Praziquantel: A Major Advance in Anthelminthic Therapy."
Reale, et al., *Brain Res.* 769(2):309-320, 1997. "The expression of a cloned *Drosophila* octopamine/tyramine receptor *Xenopus oocytes*."
Rex, et al., *J Neurochem.* 82(6):1352-1359, Sep. 2002. "Characterization of a tyramine receptor from *Caenorhabditis elegans*."
Rice, et al. (1993); Chapter 8: Structural requirements for Monoterpenoid Activity Against Insects, pp. 92-108; American Chemical Society (ACS) Symposium Series developed from a symposium sponsored by the Division of Agrochemicals at the 205th National Meeting of the American chemical society in Denver Colorado, P.A. Hedin (ed.), Mar. 28-Apr. 2, 1993.
Rice, et al., *J Econ Entomol.* 87(5):1172-1179, 1994. "Insecticidal properties of monoterpenoid derivatives to the house flv (diptera: muscidae) and red flour beetle (coleoptera: tenebrionidae)."
Robb, et al., "Agonist-specific coupling of a cloned *Drosophila* octapamine/tyramine receptor to multiple second messenger systems." *EMBO J.* Mar. 15, 1994; 13:6; 1325-1330.
Robertson, et al., *Int Rev Neurobiol.* 19:173-224, 1976. "Octopamine and some related noncatecholic amines in invertebrate nervous systems."
Roeder, *Life Sci.* 50(1):21-28, 1992. "A new octopamine receptor class in locust nervous tissue, the octopamine 3 (OA3) receptor."
Roeder, *Comp Biochem Physiol.* Part C, 107(1):1-12, 1994. Biogenic amines and their receptors in insects.
Roeder, *Prog Neurobiol.* 59(5):533-561, Dec. 1999. "Octopamine in invertebrates."
Ryan, et al., *J Chem Eco.* 14(10):1965-1975, Oct. 1988. "Plant-insect coevolution and inhibition of acetylcholinesterase."
Sangwan, et al., *Pestic Sci.* 28(3):331-335, 1990. "Nematicidal activity of some essential plant oils."
Saudou, et al., "Cloning and characterization of a *Drosophila tyramine*." EMBO J., Nov. 1990; 9:11; 361-3617.
Sawamura, et al., *J Agric Food Chem.* 47(12):4868-4872, Nov. 9, 1999. "Inhibitory Effects of Citrus Essential Oils and Their Components on the Formation of N-Nitrosodimethylamine."
Shulaev, et al., *Nature*, 385(6618):718-721, Feb. 20, 1997. "Airborne signalling by methyl salicylate in plant pathogen resistance."
Tsao, et al., "Monoterpenoids and their synthetic deravatives as leads for new insect-control agents." *American Chemical Society*; Chapter 28; 1995.
Urban, et al., *EMBO J.* 18(3):512-521, Feb. 1, 1999. "An ATP-driven efflux pump is a novel pathogenicity factor in rice blast disease."
Vanden Broeck, et al., *J Neurochem.* 64(6):2387-2395, Jun. 1995. "Characterization of a cloned locust tyramine receptor cDNA by functional expression in permanently transformed *Drosophila* S2 cells."
Van Poyer, et al., *Insec Biochem Mol Biol.* 314-5):333-338, Mar. 15, 2001. "Phenolamine-dependent adenylyl cyclase activation in *Drosophila* Schneider 2 cells."
Vernier, et al., *Trends Pharmacol Sci.* 16(11):375-385, Novmeber 1995. "An evolutionary view of drug-receptor interaction: the bioamine receptor family."
Voigt, et al., Plant J. 42(3):364-375, 2005. "A secreted lipase of *Fusarium graminearum* is a virulence factor required for infection of cereals."
Von Nickisch-Rosenegk, et al., *Insect Biochem Mol Biol.* 26(8-9):817-827, Sep.-Oct. 1996. "Cloning of biogenic amine receptors from moths (*Bombyx mori* and *Heliothis virescens* )."
Wetzel et al., *PHAS* 98(16):9377-9380, Jul. 31, 2001.
Yu, *Parasitol Research.* 88(5):412-420, Feb. 6, 2002. "A common oocyst surface antigen of *Cryptosporidium* recognized by monoclonal antibodies."
Third Office Action of the SIPO, mailed in related Chinese Patent Application No. 200780026844.1, dated Dec. 31, 2012.

\* cited by examiner

COMPOSITIONS AND METHODS FOR CONTROLLING INSECTS

RELATED APPLICATIONS

This application claims priority from U.S. Provisional Application 60/807,600, filed Jul. 17, 2006.

FIELD OF THE INVENTION

The present invention relates to compositions and methods related to controlling insects, including compositions having a synergistic blend of ingredients.

BACKGROUND OF THE INVENTION

Various chemicals and mixtures have been studied for pesticidal activity for many years with a goal of obtaining a product which is selective for invertebrates such as insects and has little or no toxicity to vertebrates such as mammals, fish, fowl and other species and does not otherwise persist in and damage the environment.

Most of the previously known and commercialized products having sufficient pesticidal activity to be useful also have toxic or deleterious effects on mammals, fish, fowl or other species which are not the target of the product. For example, organophosphorus compounds and carbamates inhibit the activity of acetylcholinesterase in insects as well as in all classes of animals. Chlordimeform and related formamidines are known to act on octopamine receptors of insects but have been removed from the market because of cardiotoxic potential in vertebrates and carcinogenicity in animals and a varied effect on different insects. Other compounds, which can be less toxic to mammals and other non-target species, are sometimes difficult to identify.

SUMMARY OF THE INVENTION

Embodiments of the present invention include pest control blends, including, in a synergistic combination, at least two ingredients such as, for example, Lilac Flower Oil, D-Limonene, Thyme Oil, Lime Oil, Black Seed Oil, Wintergreen Oil, Linalool, Tetrahydrolinalool, Vanillin, Isopropyl myristate, Piperonal (aldehyde), Geraniol, Geraniol 60, Triethyl Citrate, Methyl Salicylate, and the like.

In some embodiments, the pest control blend can include, in a synergistic combination, at least two of: Lilac Flower Oil, D-Limonene, Thyme Oil, and Lime Oil. The concentration of Lilac Flower Oil can be between 5% and 25%; the concentration of D-Limonene can be between 2% and 20%; the concentration of Thyme Oil can be between 2% and 25%; and the concentration of Lime Oil can be between 50% and 90%. Likewise, the concentration of Lilac Flower Oil can be between 10% and 15%; the concentration of D-Limonene can be between 5% and 15%; the concentration of Thyme Oil can be between 5% and 15%; and the concentration of Lime Oil can be between 60% and 80%. Further, the concentration of Lilac Flower Oil can be 12.94%; the concentration of D-Limonene can be 8.72%; the concentration of Thyme Oil can be 9.58%; and the concentration of Lime Oil can be 68.76%.

In other embodiments, pest control blend can include, in a synergistic combination, at least two of: Black Seed Oil, Linalool, Tetrahydrolinalool, Vanillin, Isopropyl myristate, Piperonal (aldehyde), and Geraniol. The concentration of Black Seed Oil can be between 5% and 70%; the concentration of Linalool can be between 2% and 25%; the concentration of Tetrahydrolinalool can be between 2% and 30%; the concentration of Vanillin can be between 0.1% and 5%; the concentration of Isopropyl myristate can be between 5% and 40%; the concentration of Piperonal (aldehyde) can be between 1% and 15%; and the concentration of Geraniol can be between 1% and 20%. Likewise, the concentration of Black Seed Oil can be between 15% and 60%; the concentration of Linalool can be between 5% and 20%; the concentration of Tetrahydrolinalool can be between 5% and 25%; the concentration of Vanillin can be between 0.5% and 3%; the concentration of Isopropyl myristate can be between 10% and 30%; the concentration of Piperonal (aldehyde) can be between 3% and 10%; and the concentration of Geraniol can be between 5% and 15%. Further, the concentration of Black Seed Oil can be between 21.5% and 52.28%; the concentration of Linalool can be between 9.63% and 15.8%; the concentration of Tetrahydrolinalool can be between 11.57% and 19.0%; the concentration of Vanillin can be between 1.12% and 1.9%; the concentration of Isopropyl myristate can be between 14.26% and 23.4%; the concentration of Piperonal (aldehyde) can be between 4.75% and 7.8%; and the concentration of Geraniol can be between 6.38% and 10.5%.

In another embodiment, the pest control blend can include in a synergistic combination, Lilac Flower Oil and Black Seed Oil. The concentration of Lilac Flower Oil can be between 40% and 90%, and the percentage of Black Seed Oil can be between 5% and 70%. Likewise, the concentration of Lilac Flower Oil can be between 45% and 85%, and the percentage of Black Seed Oil can be between 15% and 60%. Further, the concentration of Lilac Flower Oil can be between 50.13% and 80.09%, and the percentage of Black Seed Oil can be between 19.91% and 49.87%.

In yet another embodiment, the pest control blend can include, in a synergistic combination, at least two of: Thyme Oil, Wintergreen Oil, and Isopropyl myristate. The concentration of Thyme Oil can be between 25% and 55%%; the concentration of Wintergreen Oil can be between 10% and 40%; and the concentration of Isopropyl myristate can be between 20% and 50%. Likewise, the concentration of Thyme Oil can be between 35% and 45%%; the concentration of Wintergreen Oil can be between 20% and 30%; and the concentration of Isopropyl myristate can be between 30% and 40%. Further, concentration of Thyme Oil can be 39.24%; the concentration of Wintergreen Oil can be 24.82%; and the concentration of Isopropyl myristate can be 35.94%.

In other embodiments, the pest control blend can include, in a synergistic combination, at least two of: Thyme Oil, Wintergreen Oil, and Methyl Salicylate. The concentration of Thyme Oil can be between 5% and 35%; the concentration of Wintergreen Oil can be between 30% and 60%; and the concentration of Methyl Salicylate can be between 30% and 60%. Likewise, the concentration of Thyme Oil can be between 15% and 25%; the concentration of Wintergreen Oil can be between 40% and 50%; and the concentration of Methyl Salicylate can be between 40% and 50%. Further, the concentration of Thyme Oil can be 20.6%; the concentration of Wintergreen Oil can be 45.1%; and the concentration of Methyl Salicylate can be 45.1%.

The pest control blends of the invention can have a coefficient of synergy of at least 1.5 for each active ingredient, as measured by a test on a target organism, wherein the test can be selected from: knockdown time, killing time, repellency, and residual effectiveness. Likewise, the coefficient of synergy can be at least 5, or at least 10, or at least 25, for at least one active ingredient.

In some embodiments, exposure to the blend disrupts cellular calcium levels within the target organism, and/or exposure to the blend disrupts cyclic AMP levels within cells of the target organism. In some embodiments, exposure to the blend can result in binding of a receptor of the olfactory cascade of the target organism. In some embodiments, one or more components of the blend can act as an agonist or antagonist on the receptor of the target organism. Some blends include at least three active ingredients, or at least four active ingredients.

Embodiments of the invention also provide pest control formulations, including any of the blends of the invention. The pest control formulation can include at least one ingredient such as, for example, Hercolyn D, Mineral Oil, Soy Bean Oil, Piperonyl Alcohol, Ethyl Linalool, Hedione, Dipropylene glycol, Citral, gamma-terpinene, Sodium Lauryl Sulfate, Thymol, Alpha-Pinene, alpha-Terpineol, Terpinolene, Para-Cymene, Trans-Anethole, Linalyl Acetate, Beta Pinene, Camphor Dextro, Terpinene-4-ol, Span 80, Tween 80, Potassium Sorbate, Sodium Benzoate, Isopar M, BHA, BHT, dl-alpha-tocopherol lineaolate, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, Polyglycerol-4-oleate, Tocopherol Gamma Tenox, Xanthan Gum, A45 Propellent, Lecithin, a propellent, water, a surfactant, a cationic agent, Sodium Benzoate, Xanthan, Ksorbate, and the like.

In other embodiments, the invention provides methods of making a synergistic pest control formulation having desirable environmental properties. The methods can include the steps of: selecting an ingredient from a group of candidate ingredients known or believed to be generally safe for use in contact with vertebrates; screening the ingredient for binding to a G protein-coupled receptor of an invertebrate, wherein the binding results in measurable disruption of cellular calcium or cyclic AMP; combining the screened ingredient with at least one other screened ingredient, wherein the ingredients, in combination, are synergistic in an effect against a target organism. The receptor can be a receptor of the insect olfactory cascade, including, for example, a tyramine receptor, an octopamine receptor, olfactory receptor Or83b, olfactory receptor 43a, and the like.

DESCRIPTION OF EXEMPLARY
EMBODIMENTS OF THE INVENTION

Embodiments of the invention are directed to compositions for controlling insects and methods for using these compositions. Embodiments of the invention include compositions for controlling insects, which can include one or more plant essential oils and methods for using these compositions. The plant essential oils, when combined, can have a synergistic effect. The compositions also can include a fixed oil, which is typically a non-volatile non-scented plant oil. Additionally, in some embodiments, these compositions can be made up of generally regarded as safe (GRAS) compounds.

For purposes of simplicity, the term "insect" shall be used in this application; however, it should be understood that the term "insect" refers, not only to insects, but also to mites, spiders, and other arachnids, larvae, and like invertebrates. Also for purposes of this application, the term "insect control" shall refer to having a repellant effect, a pesticidal effect, or both. "Repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition. "Pesticidal effect" is an effect wherein treatment with a composition causes at least about 1% of the insects to die. In this regard, an LC1 to LC100 (lethal concentration) or an LD1 to LD100 (lethal dose) of a composition will cause a pesticidal effect. In some embodiments, the pesticidal effect is an effect wherein treatment with a composition causes at least about 5% of the exposed insects to die.

In some embodiments, the pesticidal effect is an effect wherein treatment with a composition causes at least about 10% of the exposed insects to die. In some embodiments, the pesticidal effect is an effect wherein treatment with a composition causes at least about 25% of the insects to die. In some embodiments the pesticidal effect is an effect wherein treatment with a composition causes at least about 50% of the exposed insects to die. In some embodiments the pesticidal effect is an effect wherein treatment with a composition causes at least about 75% of the exposed insects to die. In some embodiments the pesticidal effect is an effect wherein treatment with a composition causes at least about 90% of the exposed insects to die.

In some embodiments of the invention, treatment with compositions of the invention will result in a knockdown of the insects occurring within a few seconds to a few minutes. "Knockdown" is an effect wherein treatment with a composition causes at least about 1% to display reduced mobility. In some embodiments, the knockdown is an effect wherein treatment with a composition causes at least about 50% of the exposed insects to die.

The compositions of the present invention can be used to control insects by either treating a host directly, or treating an area in which the host will be located, for example, an indoor living space, outdoor patio or garden. For purposes of this application, host is defined as a plant, human or other animal.

Treatment can include use of a oil-based formulation, a water-based formulation, a residual formulation, and the like. In some embodiments, combinations of formulations can be employed to achieve the benefits of different formulation types.

Embodiments of the invention are directed to compositions for controlling insects and methods for using these compositions. Compositions of the present invention can include any of the following oils, or mixtures thereof.

Methyl salicylate, also known as *betula* oil. Methyl salicylate is a major component of oil of wintergreen and is sometimes referred to interchangeably with oil of wintergreen. It is a natural product of many species of plants, is the methyl ester of salicylic acid, and can be produced chemically from the condensation reaction of salicylic acid and methanol. Some of the plants producing it are called wintergreens, hence the common name. Methyl salicylate can be used by plants as a pheromone to warn other plants of pathogens (Shulaev, et al. (Feb. 20, 1997) *Nature* 385: 718-721). The release of methyl salicylate can also function as an exopheromone aid in the recruitment of beneficial insects to kill the herbivorous insects (James, et al. (August 2004) *J. Chem. Ecol.* 30(8): 1613-1628). Numerous plants produce methyl salicylate including species of the family *Pyrolaceae* and of the genera *Gaultheria* and *Betula*. It is noted that, where a given blend or formulation or other composition is disclosed herein as containing wintergreen oil, an alternative embodiment, containing methyl salicylate in place of wintergreen oil, is also contemplated. Likewise, where a blend or formulation of other composition includes methyl salicylate, an alternative embodiment, containing wintergreen oil, is also contemplated.

Thyme Oil is a natural product that can be extracted from certain plants, including species from the *Labiatae* family; for example, thyme oil can be obtained from *Thymus vulgaris* (also known as, *T. ilerdensis, T. aestivus*, and *T. velantianus*).

Thymol is a monoterpene phenol derivative of cymene, $C_{10}H_{13}OH$, isomeric with carvacrol, found in thyme oil, and extracted as a white crystalline substance.

Geraniol, also called rhodinol, is a monoterpenoid and an alcohol. It is the primary part of oil-of-rose and palmarosa oil. It is used in perfumes and as a flavoring. It is also produced by the scent glands of honey bees to help them mark nectar-bearing flowers and locate the entrances to their hives. Geraniol can be obtained, for example, as Geraniol 60, Geraniol 85, and Geraniol 95. When Geraniol is obtained as Geraniol 60, Geraniol 85, or Geraniol 95, then about forty percent, fifteen percent, or five percent of the oil can be Nerol. Nerol is a monoterpene ($C_{10}H_{18}O$), which can be extracted from attar of roses, oil of orange blossoms and oil of lavender.

Vanillin is the primary component of the extract of the vanilla bean. Synthetic vanillin is used as a flavoring agent in foods, beverages, and pharmaceuticals.

Other ingredients, including but not limited to black seed oil, borneol, camphene, carvacrol, β-caryophyllene, triethyl-citrate, p-cymene, hedion, heliotropine, hercolyn D, lilac flower oil, lime oil, limonene, linalool, ethyl-linalool, tetrahydro-linanool, α-pinene, β-pinene, piperonal, piperonyl alcohol, α-terpinene, tert-butyl-p-benzoquinone, α-thujene, and triethyl citrate can also be included in the compositions of the present invention.

In certain exemplary compositions of the invention that include lilac flower oil, one or more of the following compounds can be substituted for the lilac flower oil: tetrahydro-linalool; ethyl linalool; heliotropine; hedion; hercolyn D; and triethyl citrate. In certain exemplary compositions of the invention that include black seed oil, one or more of the following compounds can be substituted for the black seed oil: alpha-thujene: alpha-pinene; Beta-pinene; p-cymene; limonene; and tert-butyl-p-benzoquinone. In certain exemplary compositions of the invention that include thyme oil, one or more of the following compounds can be substituted for the thyme oil: thymol, α-thujone; α-pinene, camphene, β-pinene, p-cymene, α-terpinene, linalool, borneol, β-caryophyllene, and carvacrol. In certain exemplary embodiments of the invention that include methyl salicylate, oil of wintergreen can be substituted for the methyl salicylate. In certain exemplary embodiments of the invention that include oil of wintergreen, methyl salicylate can be substituted for the oil of wintergreen.

Oils used to prepare the exemplary compositions of the present invention can be obtained, for example, from the following sources: Millennium Specialty Chemical (Jacksonville, Fla.), Ungerer Company (Lincoln Park, N.J.), SAFC (Milwaukee, Wis.), and IFF Inc. (Hazlet, N.J.).

Exemplary embodiments of the invention also can include isopropyl myristate, which is an ester of isopropyl alcohol and myristic acid, is used as a thickening agent and emollient.

In those compositions including more than one oil, each oil can make up between about 0.1%, or less, to about 99%, or more, by weight, of the composition mixture. For example, one composition of the present invention comprises about 1% thymol and about 99% geraniol. Optionally, the compositions can additionally comprise a fixed oil, which is a non-volatile non-scented plant oil. Fixed oils useful in the formulations of the present invention include, but are not limited to, castor oil, corn oil, cumin oil, mineral oil, olive oil, peanut oil, safflower oil, sesame oil, and soy bean oil.

In certain exemplary embodiments, insect control compositions according to the invention include at least one of methyl salicylate, thyme oil, thymol, and/or geraniol. In other exemplary embodiments, insect control compositions include at least two of methyl salicylate, thyme oil, thymol, and/or geraniol. In other exemplary embodiments, insect control compositions according to the invention include methyl salicylate, thymol, and geraniol.

While embodiments of the invention can include active ingredients, carriers, inert ingredients, and other formulation components, preferred embodiments begin with a primary blend. A primary blend is preferably a synergistic combination containing two or more active ingredients and, optionally, additional ingredients. The primary blends can then be combined with other ingredients to produce a formulation. Accordingly, where concentrations, concentration ranges, or amounts, are given herein, such quantities typically are in reference to a primary blend or blends. Thus, when a primary blend is further modified by addition of other ingredients to produce a formulation, the concentrations of the active ingredients are reduced proportional to the presence of other ingredients in the formulation.

In preferred blends, methyl salicylate can be included at a concentration of between 10% or less to 60% or more; at a concentration of between 15%-50%; at a concentration of between 20%-45%; or at a concentration of about 39% by weight.

Thymol can be included at a concentration of between 5% or less to 40% or more; at a concentration of between 15%-25%; or at a concentration of about 20% by weight.

Thyme Oil can be included at a concentration of between 5% or less to 40% or more, at a concentration of between 15%-25%, or at a concentration of about 20% by weight.

Geraniol can be included at a concentration of between 5% or less to 40% or more, at a concentration of 15%-25%, or at a concentration of about 20% by weight.

In certain exemplary embodiments, the following active ingredients can be provided at the following concentrations, expressed as a percentage by weight 39% Methyl salicylate; 20% Thymol (crystal); and 20% Geraniol 60. In other exemplary embodiments, the following active ingredients can be provided at the following concentrations: 39% Methyl salicylate; 20% Thyme Oil; and 20% Geraniol 60. In other exemplary embodiments, the following active ingredients can be provided at the following concentrations: 39% Methyl salicylate; 20% Thyme Oil; and 20% Geraniol 85. In other exemplary embodiments, the following active ingredients can be provided at the following concentrations: 39% Methyl salicylate; 20% Thyme Oil; and 20% Geraniol 95. Other exemplary embodiments are shown in the tables provided below.

In exemplary embodiments, the insect control formulation also includes isopropyl myristate at a concentration of between 10-30%, more preferably 15-25%, and most preferably about 20%. Vanillin is included, preferably at a concentration between 0.5 and 4%, most preferably about 1%.

In exemplary embodiments of the invention, thymol is present in crystal form. By using the crystal form, the more volatile components of the insect control composition are stabilized and remain in the area requiring insect control for a longer period. This is explained in U.S. Provisional Application No. 60/799,434, filed May 10, 2006 which is incorporated in its entirety herein by reference. Of course, other components can be included to stabilize the insect control composition. The stabilizer can be a crystal powder, dust, granule or other form which provides an absorption surface area for the insect control composition. Other plant essential oils that are crystalline at room temperature and can be used as stabilizers in formulations of the invention include but are not limited to cinnamic alcohol crystals, salicylic acid crystals, cedrol crystals, piperonal crystals, piperonyl alcohol crystals, (s)-cis-verbenol crystals and DL-menthol crystals which are all crystalline at room temperature. Another stabilizer that can be used is a crystal of Winsense WS-3, cyclohexanecarboxamide, N-methyl-2-(1-methylethyl) and Winsense WE-23, (N-2,3-trimethyl-2-isopropylbutamide) and the like. Another useful stabilizer is talc powder.

In order to produce the stabilized formulation, the stabilizer and the insect-control composition are mixed to allow the stabilizer to become coated with the composition as described in U.S. Provisional Application No. 60/799,434, mentioned above.

The compositions of the present invention can comprise, in admixture with a suitable carrier and optionally with a suitable surface active agent, plant essential oil compounds and/or derivatives thereof, natural and/or synthetic, including racemic mixtures, enantiomers, diastereomers, hydrates, salts, solvates and metabolites, etc.

A suitable carrier can include any carrier in the art known for plant essential oils, provided the carrier does not adversely effect the compositions of the present invention. The term "carrier" as used herein means an inert or fluid material, which can be inorganic or organic and of synthetic or natural origin, with which the active compound is mixed or formulated to facilitate its application to the container or carton or other object to be treated, or to facilitate its storage, transport and/or handling. In general, any of the materials customarily employed in formulating repellents, pesticides, herbicides, or fungicides, are suitable. The compositions of the present invention can be employed alone or in the form of mixtures with such solid and/or liquid dispersible carrier vehicles and/or other known compatible active agents such as other repellants, pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The compositions of the present invention can be formulated or mixed with, if desired, conventional inert pesticide diluents or extenders of the type usable in conventional insect control agents, e.g., conventional dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

The compositions of the present invention can further comprise surface-active agents. Examples of surface-active agents that can be employed with the present invention, include emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents such as lignin, sulfite waste liquors, methyl cellulose, etc.

In some embodiments, water-based formulations are preferred. Although oil-based formulations of insect-control agents are generally more effective, water-based formulations have the advantage that they do not leave behind an oily residue on treated surfaces. Preparation of Water-Based Formulations for Insect Control are Disclosed in U.S. Provisional Application No. 60/747,592, filed May 18, 2006, which is incorporated in its entirety herein by reference.

In certain embodiments, water-based formulations are provided wherein water and a surfactant comprise between about 1% to about 99%, by weight, of the composition mixture. For example, one composition of the present invention comprises about 1% water and surfactant and about 99% of a composition, including: about 39% Methyl salicylate; about 20% Thymol (crystal); about 20% Geraniol 60; and about 1% Vanillin. For another example, one composition of the present invention comprises about 50% water and surfactant and about 50% of a composition, including: about 39% Methyl salicylate; about 20% Thymol (crystal); about 20% Geraniol 60; and about 1% Vanillin.

The compositions of the present invention can be used to control insects by either treating a host directly, or treating an area in which the host will be located. For example, the host can be treated directly by using a cream or spray formulation, which can be applied externally or topically, e.g., to the skin of a human. A composition can be applied to the host, for example, in the case of a human, using formulations of a variety of personal products or cosmetics for use on the skin or hair. For example, any of the following can be used: fragrances, colorants, pigments, dyes, colognes, skin creams, skin lotions, deodorants, talcs, bath oils, soaps, shampoos, hair conditioners and styling agents.

In the case of an animal, human or non-human, the host can also be treated directly by using a formulation of a composition that is delivered orally. For example, a composition can be enclosed within a liquid capsule and ingested.

An area can be treated with a composition of the present invention, for example, by using a spray formulation, such as an aerosol or a pump spray, or a burning formulation, such as a candle or a piece of incense containing the composition. Of course, various treatment methods can be used without departing from the spirit and scope of the present invention. For example, compositions can be comprised in household products such as: air fresheners (including heated air fresheners in which insect repellent substances are released upon heating, e.g., electrically, or by burning); hard surface cleaners; or laundry products (e.g., laundry detergent-containing compositions, conditioners).

Surprisingly, by blending certain compounds in certain relative amounts, the resulting composition demonstrates a repellant or pesticidal effect that exceeds the repellant or pesticidal effect of any component of the composition. As used herein, "component of a composition" refers to a compound, or a subset of compounds included in a composition, e.g., the complete composition minus at least one compound. As used herein, "repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition. As used herein, "pesticidal effect" is an effect wherein treatment with a composition causes at least about 1% of the insects to die. In this regard, when a first effect and a second effect are compared, the first effect can indicate a greater pesticidal or repellant efficacy if it exceeds the second effect. For example, when the effect being measured is a % killing of target insects, a greater % killing is a pesticidal effect that exceeds a lesser % killing. Effects that can be measured include, but are not limited to: time to kill a given percentage of a target insect, or repellency as to a given percentage of a target insect.

As used herein, "synergy" and "synergistic effect" can refer to any substantial enhancement, in a composition of at least two compounds, of a measurable effect, e.g., an antiparasitic effect, when compared with the effect of a component of the composition, e.g., one active compound alone, or the complete blend of compounds minus at least one compound. Synergy is a specific feature of a blend of compounds, and is above any background level of enhancement that would be due solely to, e.g., additive effects of any random combination of ingredients.

In some embodiments, a substantial enhancement of a measurable effect can be expressed as a coefficient of synergy. A coefficient of synergy is an expression of a comparison between measured effects of a composition and measured effects of a comparison composition. The comparison composition can be a component of the composition. In some embodiments, the synergy coefficient can be adjusted for differences in concentration of the complete blend and the comparison composition.

Synergy coefficients can be calculated as follows. An activity ratio (R) can be calculated by dividing the % effect of the composition ($A_B$) by the % effect of the comparison composition ($X_n$), as follows:

$$R = A_B/X_n \qquad \text{Formula 1}$$

A concentration adjustment factor (F) can be calculated based on the concentration ($C_n$), i.e., % (wt/wt) or % (vol/vol), of the comparison composition in the composition, as follows:

$$F = 100/Cn \qquad \text{Formula 2}$$

The synergy coefficient (S) can then be calculated by multiplying the activity ratio (R) and the concentration adjustment factor (F), as follows:

$$S = (R)(F) \qquad \text{Formula 3}$$

As such, the synergy coefficient (S) can also by calculated, as follows:

$$S = [(AB/Xn)(100)]/Cn \qquad \text{Formula 4}$$

In Formula 4, AB is expressed as % effect of the blend, Xn is expressed as % effect of the comparison composition (Xn), and Cn is expressed as % (wt/wt) or % (vol/vol) concentration of the comparison composition in the blend.

In some embodiments, a coefficient of synergy of about 1.1, 1.2, 1.3, 1.4, or 1.5 can be substantial and commercially desirable. In other embodiments, the coefficient of synergy can be from about 1.6 to about 5, including but not limited to about 1.8, 2.0, 2.5, 3.0, 3.5, 4.0, and 4.5. In other embodiments, the coefficient of synergy can be from about 5 to 50, including but not limited to about 10, 15, 20, 25, 30, 35, 40, and 45. In other embodiments, the coefficient of synergy can be from about 50 to about 500, or more, including but not limited to about 50, 75, 100, 125, 150, 200, 250, 300, 350, 400, and 450. Any coefficient of synergy above 500 is also contemplated within embodiments of the compositions.

Given that a broad range of synergies can be found in various embodiments described herein, it is expressly noted that a coefficient of synergy can be described as being "greater than" a given number and therefore not necessarily limited to being within the bounds of a range having a lower and an upper numerical limit. Likewise, in some embodiments described herein, certain low synergy coefficients, or lower ends of ranges, are expressly excluded. Accordingly, in some embodiments, synergy can be expressed as being "greater than" a given number that constitutes a lower limit of synergy for such an embodiment. For example, in some embodiments, the synergy coefficient is equal to or greater than 25; in such an embodiment, all synergy coefficients below 25, even though substantial, are expressly excluded.

In some embodiments, synergy or synergistic effect associated with a composition can be determined using calculations similar to those described in Colby, S. R., "Calculating Synergistic and Antagonistic Responses of Herbicide Combinations," Weeds, 1967 15:1, pp. 20-22, which is incorporated herein by reference. In this regard, the following formula can be used to express percent effect (E) of a composition including two compounds, Compound X and Compound Y:

$$E = X+Y-(X*Y/100) \qquad \text{Formula 5}$$

In Formula 5, X is the measured actual percent effect of Compound X in the composition, and Y is the measured actual percent effect of Compound Y in the composition. The expected percent effect (E) of the composition is then compared to a measured actual percent effect (A) of the composition. If the actual percent effect (A) that is measured differs from the expected percent effect (E) as calculated by the formula, then the difference is due to an interaction of the compounds. Thus, the composition has synergy (a positive interaction of the compounds) when A>E. Further, there is a negative interaction (antagonism) when A<E.

Formula 5 can be extended to account for any number of compounds in a composition; however it becomes more complex as it is expanded, as is illustrated by the following formula for a composition including three compounds, Compound X, Compound Y, and Compound Z:

$$E = X+Y+Z-((XY+XZ+YZ)/100)+(X*Y*Z/1000) \qquad \text{Formula 6}$$

An easy-to-use formula that accommodates compositions with any number of compounds can be provided by modifying Formulas 5 and 6. Such a modification of the formula will now be described. When using Formulas 5 and 6, an untreated control value (untreated with composition or compound) is set at 100%, e.g., if the effect being measured is the amount of target insects killed, the control value would be set at 100% survival of the target insect. In this regard, if treatment with compound A results in 80% killing of the target insect, then the treatment with compound A can be said to result in a 20% survival, or 20% of the control value. The relationship between values expressed as a percent effect and values expressed as a percent-of-control are set forth in the following formulas, where E' is the expected percent of control of the composition, $X_n$ is the measured actual % effect of an individual compound (Compound $X_n$) of the composition, $X_n'$ is the percent of control of an individual compound of the composition, and A' is the actual measured percent of control of the composition.

$$E = 100-E' \qquad \text{Formula 7}$$

$$X_n = 100-X_n' \qquad \text{Formula 8}$$

$$A = 100-A' \qquad \text{Formula 9}$$

By substituting the percent-of-control values for the percent effect values of Formulas 5 and 6, and making modifications to accommodate any number (n) of compounds, the following formula is provided for calculating the expected % of control (E') of the composition:

$$E' = \left(\prod_{i=1}^{n} X_i'\right) \div 100^{n-1}$$ Formula 10

According to Formula 10, the expected % of control (E') for the composition is calculated by dividing the product of the measured actual % of control values ($X_n'$) for each compound of the composition by $100^{n-1}$. The expected % of control (E') of the composition is then compared to the measured actual % of control (A') of the composition. If the actual % of control (A') that is measured differs from the expected % of control (E') as calculated by the Formula 10, then the difference is due to an interaction of the compounds. Thus, the composition has synergy (a positive interaction of the compounds) when A'<E'. Further, there is a negative interaction (antagonism) when A'>E'.

Compositions containing two or more compounds in certain ratios or relative amounts can be tested for a synergistic effect by comparing the pesticidal effect of a particular composition of compounds to the pesticidal effect of a component of the composition. Additional information related to making a synergy determination can be found in the examples set forth in this document. While synergy has been described in terms of a coefficient of synergy and in terms of the Colby synergy calculations, it is noted that synergy by other measures or determinations known in the art is, in some embodiments, also within the meaning of synergy as described and claimed herein.

In embodiments of the present invention, a *Drosophila* Schneider 2 cell line is stably transfected with a G protein-coupled receptor that is amplified from *Drosophila melanogaster* head cDNA phage library. The cell line can be used to screen potential active ingredients, as described below.

Receptor binding can result in cellular changes down stream to the receptor. The subsequent cellular changes may include altered intracellular cAMP levels, calcium levels or both.

In some embodiments of the invention, the screening method for insect control activity can target an insect olfactory receptor protein. The insect olfactory system includes more than 60 identified olfactory receptors. These receptors are generally members of a large family of G protein coupled receptors (GPCRs).

In *Drosophila melanogaster*, the olfactory receptors are located in two pairs of appendages located on the head of the fly. The family of *Drosophila* chemoreceptors includes approximately 62 odorant receptor (Or) and 68 gustatory receptor (Gr) proteins, encoded by families of approximately 60 Or and 60 Gr genes through alternative splicing. Some of these receptor proteins have been functionally characterized, while others have been identified by sequence homology to other sequences but have not been fully characterized. Other insects have similar olfactory receptor proteins.

In certain embodiments, the insect olfactory receptor protein targeted by the screening or insect control method of the invention is the tyramine receptor (tyrR). In additional embodiments, the insect olfactory receptor protein is the insect olfactory receptor protein Or83b or Or43a. In additional embodiments, the targeted protein can be any of the insect olfactory protein receptors.

Additionally, other components of the insect olfactory receptor cascade can be targeted using the method of the invention in order to identify useful insect control compounds. Exemplary insect olfactory cascade components that can be targeted by methods of the invention include but are not limited to serotonin receptor, Or22a, Or22b, Gr5a, Gr21a, Gr61a, beta-arrestin receptor, GRK2 receptor, and tyramine beta-hydroxylase receptor, and the like.

The methods of embodiments of the invention can used to control any type of insect. Exemplary insects that can be controlled include but are not limited to beetles, cockroaches, flies, ants, insect larvae, bees, lice, fleas, mosquitoes, moths, and the like. Exemplary insect orders can include but are not limited to Anoplura, Orthoptera, Hemiptera, Ephemeroptera, Strepsiptera, Diptera, Dermaptera, Diplura, Dictyoptera, Collembola, Coleoptera, Neuroptera, Thysanoptera, Mecoptera, Lepidoptera, Ephemeroptera, Plecoptera, Embioptera, Trichoptera, Hymenoptera, Psocoptera, Phasmida, Protura, Thysanura, Mecoptera, Isoptera, Siphonaptera, Mallophaga, Lepidoptera, and the like.

Any insect cell or cell line can be used for the screening assay. Exemplary insect cell lines include but are not limited to SF9, SF21, T.ni, *Drosophila* S2 cells, and the like. Methods of culturing the insect cells are known in the art, and are described, for example, in Lynn et al., J. Insect Sci. 2002; 2: 9, incorporated herein by reference in its entirety. Methods of starting a new insect cell culture from a desired insect cell are described, for example, in Lynn et al. Cytotechnology. 1996; 20:3-1 1, which is incorporated herein by reference in its entirety.

Further discussion of various approaches to screening, preparing, evaluating, and using insect control formulations are disclosed in the following applications, each of which is incorporated by reference in its entirety: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; U.S. Provisional Application 60/807,600, entitled COMPOSITIONS AND METHODS FOR CONTROLLING INSECTS; U.S. Provisional Application 60/805,963, entitled COMPOSITIONS FOR TREATING PARASITIC INFECTIONS AND METHODS OF SCREENING FOR SAME; U.S. Provisional Application 60/718,570, entitled COMPOSITIONS HAVING INSECT CONTROL ACTIVITY AND METHODS FOR USE THEREOF.

The present invention is further illustrated by the following examples.

EXAMPLES

Various exemplary compositions containing plant essential oils have been prepared and tested for efficacy against different targets including insects, spiders, and fungi.

The following examples provide details of certain exemplary compositions, with certain corresponding data being provided in Exhibit A. As disclosed herein, it is within the scope of the present invention to vary the concentrations of components of each composition within useful ranges. Accordingly, these specific compositions are merely representative of certain embodiments of the invention.

Example 1

25b4a Oil-based Compositions

Composition are prepared having the ingredients and ratios as specified in the following table:

| 25b4a Compositions | | | | | | | | | | |
|---|---|---|---|---|---|---|---|---|---|---|
| | % (by Weight) | | | | | | | | | |
| | 25b4a V#1 | 25b4a V#2 | 25b4a V#3 | 25b4a V#4 | 25b4a V#5 | 25b4a V#6 | 25b4a V#7 | 25b4a V#8 | 25b4a V#9 | 25b4a V#10 |
| Methyl Salicylate | 39 | 39 | 39 | 20 | 39 | 39 | 39 | 39 | 20 | 39 |
| Thymol (crystal) | 20 | 20 | 20 | 39 | 20 | | | | | |
| Thyme Oil | | | | | | 20 | 20 | 20 | 39 | 20 |
| Geraniol 60 | 20 | | | | | 20 | | | | |
| Geraniol 85 | | 20 | | | | | 20 | | | |
| Geraniol 95 | | | 20 | | | | | 20 | | |
| Isopropyl myristate | 20 | 20 | 20 | 40 | 40 | 20 | 20 | 20 | 40 | 40 |
| Vanillin | 1 | 1 | 1 | 1 | 1 | 1 | 1 | 1 | 1 | 1 |

The compositions are tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. For testing purposes, one (1) gallon of the formulation is applied to 1000 ft² of surface area and allowed to dry for two (2) hours. Insects are then introduced to the surface area. Data corresponding to such test(s) are provided in the table below. The following table shows results for a 25b4a oil-based composition applied to a stainless steel surface.

| Flour BeetleData Details of Mixtures: 25b4a oil formulation @1 gal/1000 sq ft pipetted onto SS surface and allowed to dry 2 hrs Test: On Stainless Steel | | | | |
|---|---|---|---|---|
| Treatment | 30 min | 1 hr | 2 hr | 4 hr |
| A: Alive | 0 | 0 | 0 | 0 |
| KD | 0 | 0 | 0 | 0 |
| Dead | 10 | 10 | 10 | 10 |
| B: Alive | 0 | 0 | 0 | 0 |
| KD | 0 | 0 | 0 | 0 |
| Dead | 10 | 10 | 10 | 10 |
| C: Alive | 0 | 0 | 0 | 0 |
| KD | 0 | 0 | 0 | 0 |
| Dead | 10 | 10 | 10 | 10 |
| D: Alive | 2 | 1 | 1 | 0 |
| KD | 0 | 0 | 0 | 1 |
| Dead | 8 | 9 | 9 | 9 |
| Ave Dead | 95% | 98% | 98% | 98% |

Example 2

25b4a Water-based Composition

Compositions are prepared having the ingredients and ratios as specified in the following table, which compositions have the same ingredients as those of Example 1, combined in a 1:1 ratio with a mixture of water and a small amount of (less than 1%) surfactant.

| 25b4a Water-Based Compositions | | | | | | | | | | |
|---|---|---|---|---|---|---|---|---|---|---|
| | % (by Weight) | | | | | | | | | |
| | 25b4a WB V#1 | 25b4a WB V#2 | 25b4a WB V#3 | 25b4a WB V#4 | 25b4a WB V#5 | 25b4a WB V#6 | 25b4a WB V#7 | 25b4a WB V#8 | 25b4a WB V#9 | 25b4a WB V#10 |
| Methyl Salicylate | 19.5 | 19.5 | 19.5 | 1.0 | 19.5 | 19.5 | 19.5 | 19.5 | 10 | 19.5 |
| Thymol (crystal) | 10 | 10 | 10 | 19.5 | 10 | | | | | |
| Thyme Oil | | | | | | 10 | 10 | 10 | 19.5 | 10 |
| Geraniol 60 | 10 | | | | | 10 | | | | |
| Geraniol 85 | | 10 | | | | | 10 | | | |
| Geraniol 95 | | | 10 | | | | | 10 | | |
| Isopropyl myristate | 10 | 10 | 10 | 20 | 20 | 10 | 10 | 10 | 20 | 20 |
| Vanillin | 0.5 | 0.5 | 0.5 | 0.5 | 0.5 | 0.5 | 0.5 | 0.5 | 0.5 | 0.5 |
| Water and Surfactant | 50 | 50 | 50 | 50 | 50 | 50 | 50 | 50 | 50 | 50 |

The compositions are tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Data corresponding to such test(s) are provided in the table below. For testing purposes, one (1) gallon of the formulation is applied to 1000 ft² of surface area and allowed to dry for two (2) hours. Insects are then introduced to the surface area. Data corresponding to such test(s) are provided in the table below. The following table shows results for the 25b4a water-based composition applied to a stainless steel surface.

Flour Beetle Data
Details of Mixtures: 25b4a water based formulation @1 gal/1000 sq ft pipetted onto SS surface and allowed to dry 2 hrs
Test: On Stainless Steel

| Treatment | | 30 min | 1 hr | 2 hr | 4 hr |
|---|---|---|---|---|---|
| A | Alive | 0 | 0 | 0 | 0 |
|   | KD | 0 | 0 | 0 | 0 |
|   | Dead | 10 | 10 | 10 | 10 |
| B | Alive | 0 | 0 | 0 | 0 |
|   | KD | 0 | 0 | 0 | 0 |
|   | Dead | 10 | 10 | 10 | 10 |
| C | Alive | 0 | 0 | 0 | 0 |
|   | KD | 0 | 0 | 0 | 0 |
|   | Dead | 10 | 10 | 10 | 10 |
| D | Alive | 0 | 0 | 0 | 0 |
|   | KD | 0 | 0 | 0 | 0 |
|   | Dead | 10 | 10 | 10 | 10 |
| Ave Dead | | 100% | 100% | 100% | 100% |

Example 3

CL17

Compositions are prepared having the ingredients and ratios as specified in the following table:

The compositions identified as "CL17" and "CL17 New" in the table above are prepared and tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Testing shows high efficacy and synergy. In addition to containing Thyme Oil instead of Thymol, "CL17 New" includes a variant form of LFO, VI.

The composition identified in the table above as "CL17/MO" and "CL17 New/MO" include 20% mineral oil and 80% of either "CL17" and "CL17 New," respectively. The 20% mineral oil is provided as a stabilizer. The compositions are tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Testing shows high efficacy and synergy.

The composition identified in the table above as "CL17/SO" and "CL17 New/SO" include 20% safflower oil and 80% of either "CL17" and "CL17 New," respectively. The 20% safflower oil is provided as a stabilizer. The compositions are tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Testing show high efficacy and synergy.

CL17 Compositions

| | % (by Weight) | | | | | |
|---|---|---|---|---|---|---|
| Oil | CL17 | CL17/MO | CL17/SO | CL17/New | CL17 New/MO | CL17 New/SO |
| d-limonene | 83 | 66.4 (=83*0.8) | 66.4 (=83*0.8) | 83 | 66.4 (=83*0.8) | 66.4 (=83*0.8) |
| Lime Oil | 10 | 8 (=10*0.8) | 8 (=10*0.8) | 10 | 8 (=10*0.8) | 8 (=10*0.8) |
| Lilac Flower Oil (IFF) | 4 | 3.2 (=4*0.8) | 3.2 (=4*0.8) | | | |
| Lilac Flower Oil (V1) | | | | 4 | 3.2 (=4*0.8) | 3.2 (=4*0.8) |
| Thymol (crystal) | 3 | 2.4 (=3*0.8) | 2.4 (=3*0.8) | | | |
| Thyme Oil | | | | 3 | 2.4 (=3*0.8) | 2.4 (=3*0.8) |
| Mineral Oil | | 20 | | | 20 | |
| Safflower Oil | | | 20 | | | 20 |

Example 4

CL30

Composition are prepared having the ingredients and ratios as specified in the following table:

| | CL30 Compositions | | |
|---|---|---|---|
| | % (by Weight) | | |
| Oil | CL30 | CL30 R #1 | CL30 R #2 |
| Lime Oil | | 70 | 70 |
| d-limonene | 70 | 9 | |
| | | (=30*0.3) | |
| Black Seed Oil | 4.5 | | 15 |
| | (=15*0.3) | | (=50*0.3) |
| Lilac Flower Oil | 15 | 12 | 15 |
| (IFF) | (=50*0.3) | (=40*0.3) | (=50*0.3) |
| Thyme Oil | 10.5 | 9 | |
| | (=35*0.3) | (=30*0.3) | |

The CL30 Composition is prepared as follows: Step 1—mix 50% LFO (supplied by IFF; LFO is free of diethyl phthalate) with 35% thyme oil and 15% black seed oil (BSO). This initial mix is then combined in Step 2, in a 30:70 ratio, with d-limonene, such that the final mixture is 70% d-limonene and 30% of the LFO/thyme oil/BSO mixture from Step 1. The CL30 R#1 composition is prepared as follows: Step 1—mix 30% thyme oil, with 40% LFO, and 30% d-limonene. Step 2—mix the blend from Step 1 (30%) in lime oil (70%). The CL30 R#2 composition is prepared as follows: Step 1—mix 50% LFO (supplied by IFF) with 50% BSO. Step 2—mix the blend from Step 1 (30%) in lime oil (70%).

The compositions are tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Testing show high efficacy and synergy.

Example 5

LFO V4

A composition is prepared having the ingredients and ratios as specified in the following table:

| | LFO V4 Composition |
|---|---|
| Oil | % (by Weight) LFO V4 |
| Linalool | 14 |
| Tetrahydro linalool | 25 |
| Piperonal | 10 |
| Piperonyl alcohol | 10 |
| Isopropyl myristate | 20 |
| Triethyl citrate | 15 |
| Vanillin | 1 |

The composition based upon fractionated LFO is prepared, containing 14% linalool, 25% tetrahydro linalool, 10% piperonal, 10% piperonyl alcohol, 20% isopropyl myristate, 15% triethyl citrate, and 1% vanillin. The composition is tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Testing show high efficacy and synergy.

Example 6

25b E

A composition is prepared having the ingredients and ratios as specified in the following table:

| | 25bE Composition |
|---|---|
| Oil | % (by Weight) 25bE |
| d-limonene | 70 |
| Methyl salicylate | 15 |
| | (=50*0.3) |
| Thyme Oil | 15 |
| | (=50*0.3) |

The composition is prepared as follows: Step 1—mix 50% methyl salicylate (list 4a), with 50% thyme oil (list 25b). Step 2—mix the blend of Step 1 (30%) in d-limonene (70%) (list 4b). The composition was tested for efficacy against one or more of: flour beetle, Argentine ant, German cockroach, bedbug, darkling beetle, house spider, Indian meal moth, red fruit fly, *Penicillium chrysotenum*, and *Aspergillus ochraceus*; and/or for its function in one or more of: knockdown, kill, repellency, residual activity, oil-based versus water-based efficacy, speed of kill, efficacy on different surfaces, efficacy against different sexes of target organism, efficacy against different strains of target organism, and efficacy against different developmental stages of target. Testing show high efficacy and synergy.

Example 7

Composition F-4002

A blend of oils, denoted as B-5028, is prepared and set aside. The composition of this blend in weight percent format is provided below:

| B-5028 from Oils | | |
|---|---|---|
| CAS | Description | wt/wt |
| 8007-46-3 | Thyme Oil White | 20.6% |
| 68917-75-9 | Wintergreen Oil | 45.1% |
| 110-27-0 | Isopropyl myristate | 34.3% |

Using proportions in the table below, a solution is prepared of Polyglycerol-4-oleate, Lecithin and water. Then the B-5028 oil blend is added slowly above surface to this blend with mild mixing at the interface to create a concentrate denoted as F-4001.

Composition of F-4001 Concentrate
F-4001 from B-5028

| CAS | Description | wt/wt |
|---|---|---|
| 9007-48-1 | Polyglycerol-4-oleate | 0.90% |
| 8002-43-5 | Lecithin | 0.20% |
| 7732-18-5 | Water | 9.8% |
| | B-5028 | 89.1% |

The F-4001 concentrate is diluted with a mixture of potassium sorbate and xanthan gum in water in the following ratios to create the finished product F-4002 according to proportions in the table below:

Composition of F-4002 Product
F-4002 from F-4001

| CAS | Description | wt/wt |
|---|---|---|
| 590-00-1 or 24634-61-5 | Potassium Sorbate | 1.00% |
| 11138-66-2 | Xanthan Gum | 0.28% |
| 7732-18-5 | Water | 81.82% |
| | F-4001 | 16.90% |

The exploded and summarized formula for the F-4002, the 25B-4-a finished product ready for spraying, is as follows in the following table.

F4002

| CAS | Description | wt/wt |
|---|---|---|
| 8007-46-3 | Thyme Oil White | 3.09% |
| 68917-75-9 | Wintergreen Oil | 6.77% |
| 110-27-0 | Isopropyl myristate | 5.15% |
| 590-00-1 or 24634-61-5 | Potassium Sorbate | 0.11% |
| 9007-48-1 | Polyglycerol-4-oleate | 0.15% |
| 11138-66-2 | Xanthan Gum | 0.28% |
| 8002-43-5 | Lecithin or Soya Lecithin | 0.034% |
| 7732-18-5 | Water | 84.41% |

Example 8

Composition F-4010 (Methyl Salicylate Version of F-4002)

This product is identical to F-4002 except that the Wintergreen Oil is replaced with Methyl Salicylate.

A blend of oils, denoted as B-5034, is prepared and set aside. The composition of this blend in weight percent format is provided in the table below. This product can be manufactured in the following way:

Composition of B-5034 Oil Blend
B-5034 from Oils

| CAS | Description | wt/wt |
|---|---|---|
| 8007-46-3 | Thyme Oil White | 20.6% |
| 119-36-8 | Methyl Salicylate | 45.1% |
| 110-27-0 | Isopropyl myristate | 34.3% |

Using the proportions in the table below, a solution is prepared of Polyglycerol-4-oleate, Lecithin and water. Then the B-5034 oil blend is added slowly above surface to this blend with mild mixing at the interface to create a concentrate denoted as F-4009.

Composition of F-4009 Concentrate
F-4009 from B-5034

| CAS | Description | wt/wt |
|---|---|---|
| 9007-48-1 | Polyglycerol-4-oleate | 0.90% |
| 8002-43-5 | Lecithin | 0.20% |
| 7732-18-5 | Water | 9.8% |
| | B-5034 | 89.1% |

The F-4009 concentrate is diluted with a mixture of potassium sorbate and xanthan gum in water in the following ratios to create the finished product F-4010 according to proportions in the following table.

Composition of F-4010 RTU Product
F-4010 from F-4009

| CAS | Description | wt/wt |
|---|---|---|
| 590-00-1 or 24634-61-5 | Potassium Sorbate | 1.00% |
| 11138-66-2 | Xanthan Gum | 0.28% |
| 7732-18-5 | Water | 81.82% |
| | F-4009 | 16.90% |

The exploded and summarized formula for the F-4010, the 25B-3 finished product ready for spraying, is as follows in the following table.

Total composition of F-4010 RTU spray product after explosion and summarization.
F-1010 Exploded & Summarized PCT

| CAS | Description | wt/wt |
|---|---|---|
| 8007-46-3 | Thyme Oil White | 3.09% |
| 119-36-8 | Methyl Salicyate | 6.77% |
| 110-27-0 | Isopropyl myristate | 5.15% |
| 590-00-1 or 24634-61-5 | Potasium Sorbate | 0.11% |
| 9007-48-1 | Polyglycerol-4-oleate | 0.15% |
| 11138-66-2 | Xanthan Gum | 0.275 |
| 8002-43-18-5 | Lecithin or Soya Lecithin | 0.034% |
| 7732-18-5 | Water | 84.41% |

Example 9

Composition F-4007 (High Residual Version of F-4002 Made with B-5016)

This product can be manufactured in the following way: A blend of oils, denoted as B-5016, is prepared and set aside.

The composition of this blend in weight percent format is provided in the following table.

| Composition of B-5016 Oil Blend B-5016 from Oils | | |
|---|---|---|
| CAS | Description | wt/wt |
| 8007-46-3 | Thyme Oil White | 39.2% |
| 68917-75-9 | Wintergreen Oil | 24.8% |
| 110-27-0 | Isopropyl myristate | 35.9% |

Using the proportions in the table below, a solution is prepared of Polyglycerol-4-oleate, Lecithin and water. Then the B-5016 oil blend is added slowly above surface to this blend with mild mixing at the interface to create a concentrate denoted as F-4003.

| Composition of F-4003 Concentrate F-4003 from B-5016 | | |
|---|---|---|
| CAS | Description | wt/wt |
| 9007-48-1 | Polyglycerol-4-oleate | 0.90% |
| 8002-43-5 | Lecithin | 0.20% |
| 7732-18.5 | Water | 9.8% |
| | B-5016 | 89.1% |

The F-4003 concentrate is diluted with a mixture of potassium sorbate and xanthan gum in water in the following ratios to create the finished product F-4007 according to proportions in the following table.

| Composition of F-4007 RTU Product F-4007 from F-4003 | | |
|---|---|---|
| CAS | Description | wt/wt |
| 590-00-1 or 24634-61-5 | Potassium Sorbate | 1.00% |
| 11138-66-2 | Xanthan Gum | 0.28% |
| 7732-18-5 | Water | 81.8% |
| | F-4003 | 16.9% |

The exploded and summarized formula for the F-4007, the 25B-4-a finished product that has high residual ready for spraying, is as follows in the table below. This product uses B-5016, a 25B-4-a oil mix which shows high residual efficacy.

| Total composition of F-4007 RTU spray product<br>after explosion and summarization.<br>F-4007 Exploded & Summarized PCT | | |
|---|---|---|
| CAS | Description | wt/wt |
| 8007-46-3 | Thyme Oil White | 5.89% |
| 68917-75-9 | Wintergreen Oil | 3.72% |
| 110-27-0 | Isopropyl myristate | 5.39% |
| 590-00-1 or 24634-61-5 | Potasium Sorbate | 0.11% |
| 9007-48-1 | Polyglycerol-4-oleate | 0.15% |
| 11138-66-2 | Xanthan Gum | 0.275% |
| 8002-43-18-5 | Lecithin or Soya Lecithin | 0.034% |
| 7732-18-5 | Water | 84.4% |

Example 10

Composition F-4007 (B-5028 in 1% SLS & 10% Water)

A stock solution of 10% Sodium Lauryl Sulfate in water, denoted as S-1002, is prepared according to weight percentages in the table below or the solution can be purchased.

| Preparation of 10% Sodium Lauryl Sulfate in Water<br>S-1002 10% SLS Solution | | |
|---|---|---|
| CAS | Description | wt/wt |
| 151-21-3 | Sodium Lauryl Sulfate | 90% |
| 7732-18-5 | Water | 10% |

The S-1002 solution is then added to B-5028 according to weight percentages in the table below to create F-4000, B-5028 in 1% SLS.

| Preparation of F-4000 (B-5028 w 1% SLS & 10% water)<br>F-4000 B-5028 w 1% SLS & 10% water | | |
|---|---|---|
| | Description | wt/wt |
| B-5028 | 25B-4A for Institutions | 90% |
| S-1002 | Stock 10% SLS Solution | 10% |

B-5006

In some embodiments, a blend of LFO, D-Limonene, Thyme Oil White, and Lime Oil 410 is preferred. Various embodiments are directed to variations on the blend. A preferred embodiment is:

| CAS # | Ingredient | Weight % |
|---|---|---|
| | LFO | 12.94% |
| 5989-27-5 | D-Limonene | 8.72%% |
| 8007-46-3 | Thyme Oil White | 9.58% |
| | Lime Oil 410 | 68.76% |

In some embodiments, the LFO of B-5006 can be replaced by its major components, as with XL 101.

Example 11

Composition B-5008 (XL101 using 4:1 LFO to BSO)

The formulation for manufacture of B-5008, the insect repellent product containing a volumetric ratio of 4 parts LFO to 1 part BSO is provided below.

| Composition of B-5008<br>B-5008 PCT | | |
|---|---|---|
| CAS | Description | wt/wt |
| | LFO | 80.09% |
| 977017 | BSO | 19.91% |

Example 12

XL 101

In some embodiments, a blend of Lilac Flower Oil and Black Seed Oil is preferred. Various embodiments are directed to variations on the blend. For example, in some embodiments, a ratio of approximately 1:1 is desirable. Where such a ratio is based upon volume measurements, the weight/weight ratio can be somewhat more or less than exactly 1:1. In some embodiments, XL 101 1:1 can include the following ingredients:

| XL 101 1:1 - LFO | | |
|---|---|---|
| CAS # | Ingredient | Weight % |
|  | LFO | 50.13% |
| 977017-84-7 | BSO | 49.87% |

In other embodiments, LFO is replaced by a combination of other oils found in LFO, such that a 1:1 formulation includes the following ingredients:

| XL 101 1:1 - LFO modified | | |
|---|---|---|
| CAS # | Ingredient | Weight % |
| 977017-84-7 | BSO | 52.28% |
| 78-70-6 | Linalool Coeur | 9.63% |
| 78-69-3 | Tetrahydrolinalool | 11.57% |
| 121-33-5 | Vanillin | 1.12% |
| 110-27-0 | Isopropyl myristate | 14.26% |
| 120-57-0 | Piperonal (aldehyde) | 4.75% |
| 106-24-1 | Geraniol Fine FCC | 6.38% |

In still other embodiments, a ratio of 4:1 is desirable. Some embodiments of blends having this characteristic, with either LFO or LFO ingredient oils, include the ingredients found in the following three tables:

| XL 101 4:1 - LFO | | |
|---|---|---|
| CAS # | Ingredient | Weight % |
|  | LFO | 80.09% |
| 977017-84-7 | BSO | 19.91% |

| XL 101 4:1 - LFO modified A | | |
|---|---|---|
| CAS # | Ingredient | Weight % |
| 977017-84-7 | BSO | 21.50% |
| 78-70-6 | Linalool Coeur | 15.90% |
| 78-69-3 | Tetrahydrolinalool | 19.00% |
| 121-33-5 | Vanillin | 1.80% |
| 110-27-0 | Isopropyl myristate | 23.50% |
| 120-57-0 | Piperonal (aldehyde) | 7.80% |
| 106-24-1 | Geraniol Fine FCC | 10.50% |

| XL 101 4:1 - LFO modified B | | |
|---|---|---|
| CAS # | Ingredient | Weight % |
| 977017-84-7 | BSO | 21.5% |
| 78-70-6 | Linalool Coeur | 15.8% |
| 78-69-3 | Tetrahydrolinalool | 19.0% |
| 121-33-5 | Vanillin | 1.9% |
| 110-27-0 | Isopropyl myristate | 23.4% |
| 120-57-0 | Piperonal (aldehyde) | 7.8% |
| 106-24-1 | Geraniol Fine FCC | 10.5% |

Example 13

B-5016

In some embodiments, a blend of Thyme Oil White, Wintergreen Oil, and Isopropyl myristate is preferred. Various embodiments are directed to variations on the blend. In some embodiments, B-5016 can include the following ingredients:

| B-5016 | | |
|---|---|---|
| CAS # | Ingredient | Weight % |
| 8007-46-3 | Thyme Oil White | 39.24% |
| 68917-75-9 | Wintergreen Oil | 24.82% |
| 110-27-0 | Isopropyl myristate | 35.94% |

In other embodiments, B-5016 is diluted to an 89% concentration through the addition of Polyglycerol-4-oleate, Lecithin, and water to form F-4003:

| F-4003 | | |
|---|---|---|
| CAS # | Ingredient | Weight % |
| 9007-48-1 | Polyglycerol-4-oleate | 0.90% |
| 8002-43-5 | Lecithin | 0.20% |
| 7732-18-5 | water | 9.8% |
|  | B-5016 | 89.10% |

Example 14

B-5028

In some embodiments, a blend of Thyme Oil White, Wintergreen Oil, and Isopropyl myristate is preferred. Various embodiments are directed to variations on the blend. In some embodiments, B-5028 can include the following ingredients:

| B-5028 | | |
|---|---|---|
| CAS # | Ingredient | Weight % |
| 8007-46-3 | Thyme Oil White | 20.6% |
| 68917-75-9 | Wintergreen Oil | 45.1% |
| 110-27-0 | Isopropyl myristate | 34.3% |

In other embodiments, synthetic Methyl salicylate is substituted for the Wintergreen Oil, resulting in PB-5034:

| | PB-5034 | |
|---|---|---|
| CAS # | Ingredient | Weight % |
| 8007-46-3 | Thyme Oil White | 20.6% |
| | Methyl salicylate synthetic | 45.1% |
| 110-27-0 | Isopropyl myristate | 34.3% |

Example 15

B-5006

In some embodiments, a blend of LFO, D-Limonene, Thyme Oil White, and Lime Oil 410 is preferred. Various embodiments are directed to variations on the blend. A preferred embodiment is:

| CAS # | Ingredient | Weight % |
|---|---|---|
| | LFO | 12.94% |
| 5989-27-5 | D-Limonene | 8.72%% |
| 8007-46-3 | Thyme Oil White | 9.58% |
| | Lime Oil 410 | 68.76% |

In some embodiments, the LFO of B-5006 can be replaced by its major components, as with XL 101.

Example 16

Coefficient of Synergy

A blend is prepared and tested against a target organism. Likewise, each individual ingredient is also tested against the target organism. Both knockdown (KD) and kill are measured. The blends act more quickly than any individual ingredient. The ratio of time for the effect is the coefficient of synergy. For the "constant total AI amount" test, each individual ingredient was used in the same amount, as the total amount of all active ingredients within the blend. For the "constant ingredient amount" test, each ingredient was used in the same amount as that ingredient was present in the blend.

Thus, for example, if 15 mg/sq cm of the blend were applied to a test dish in each case, then for "constant total AI" 15 mg/sq cm of each individual active was also used, singly, in the comparison tests. In contrast, if chemical A was present as 10% of the blend, then in the constant ingredient amount test, chemical A was present at 1.5 mg/sq cm, 10% of the total amount of the blend administered.

| | constant total AI amount | | constant ingredient amount | |
|---|---|---|---|---|
| chemical | KD time | Synergy | KD time | Synergy |
| A | 35 | 3.5 | none | *** |
| B | 41 | 4.1 | 3900 | 390 |
| C | 150 | 15 | 3300 | 330 |
| D | >86400 | >8640 | >86400 | >8640 |
| Blend | 10 | 1 | 10 | 1 |

| | constant total AI amount | | constant ingredient amount | |
|---|---|---|---|---|
| chemical | Kill time | Synergy | Kill time | Synergy |
| A | 180 | 4.5 | 43200 | 1080 |
| B | 240 | 6 | 43200 | 1080 |
| C | 240 | 6 | 43200 | 1080 |
| D | >86400 | >2160 | >86400 | >2160 |
| Blend | 40 | 1 | 40 | 1 |

What is claimed is:

1. A pest control blend, comprising, in a synergistic combination, Thyme Oil, Wintergreen Oil, and Isopropyl myristate, wherein the concentration of Thyme Oil is between 15% and 25%; the concentration of Wintergreen Oil is between 40% and 50%; and the concentration of Isopropyl myristate is between 30% and 40%.

2. The pest control blend of claim 1, wherein the concentration of Thyme Oil is 20.6%; the concentration of Wintergreen Oil is 45.1%; and the concentration of Isopropyl myristate is 34.3%.

3. The pest control blend of claim 1, having a coefficient of synergy of at least 1.5 for each active ingredient, as measured by a test on a target organism, wherein the test is selected from: knockdown time, killing time, repellency, and residual effectiveness.

4. The pest control blend of claim 3, having a coefficient of synergy of at least 5 for at least one active ingredient.

5. The pest control blend of claim 4 having a coefficient of synergy of at least 10 for at least one active ingredient.

6. The pest control blend of claim 5, having a coefficient of synergy of at least 25 for at least one active ingredient.

7. The pest control blend of claim 1, wherein exposure to the blend disrupts cellular calcium levels within a target organism.

8. The pest control blend of claim 7, wherein exposure to the blend disrupts cyclic AMP levels within cells of the target organism.

9. The pest control blend of claim 7, wherein exposure to the blend results in binding of a receptor of the olfactory cascade of the target organism.

10. The pest control blend of claim 9, wherein one or more components of the blend act as an agonist or antagonist on the receptor of the target organism.

11. A pest control formulation, comprising the blend of claim 1.

12. The pest control formulation of claim 11, further comprising at least one ingredient selected from the group consisting of: Hercolyn D, Mineral Oil, Soy Bean Oil, Piperonyl Alcohol, Ethyl Linalool, Hedione, Dipropylene glycol, Citral, gamma-terpinene, Sodium Lauryl Sulfate, Thymol, Alpha-Pinene, alpha-Terpineol, Terpinolene, Para-Cymene, Trans-Anethole, Linalyl Acetate, Beta Pinene, Camphor Dextro, Terpinene-4-ol, Span 80, Tween 80, Potassium Sorbate, Sodium Benzoate, Isopar M, BHA, BHT, dl-alpha-tocopherol lineaolate, Alpha Terpinene, Borneol L, Camphene, Decanal, Dodecanal, Fenchol Alpha, Geranyl Acetate, Isoborneol, 2-Methyl 1,3-cyclohexadiene, Myrcene, Nonanal, Octanal, Polyglycerol-4-oleate, Tocopherol Gamma Tenox, Xanthan Gum, A45 Propellent, Lecithin, a propellent, water, a surfactant, a cationic agent, Sodium Benzoate, Xanthan, and Ksorbate.

13. A pest control blend, comprising, in a synergistic combination, thyme oil, wintergreen oil and isopropyl myristate, wherein thyme oil : wintergreen oil : isopropyl myristate occurs in a concentration ratio of 1:2.19:1.67.

* * * * *